(12) United States Patent
Macoviak et al.

(10) Patent No.: US 6,254,563 B1
(45) Date of Patent: Jul. 3, 2001

(54) PERFUSION SHUNT APPARATUS AND METHOD

(75) Inventors: John A. Macoviak, La Jolla; Wilfred J. Samson, Saratoga; James J. Leary, Sunnyvale; Brady D. Esch, San Jose, all of CA (US)

(73) Assignee: Cardeon Corporation, Cupertino, CA (US)

( * ) Notice: Subject to any disclaimer, the term of this patent is extended or adjusted under 35 U.S.C. 154(b) by 0 days.

(21) Appl. No.: 09/532,660

(22) Filed: Mar. 20, 2000

Related U.S. Application Data

(63) Continuation of application No. 09/212,580, filed on Dec. 14, 1998.
(60) Provisional application No. 60/069,490, filed on Dec. 15, 1997.

(51) Int. Cl.[7] ............................. A61M 5/00; A61M 29/00
(52) U.S. Cl. .............................. 604/8; 604/96; 604/101; 604/104; 606/194
(58) Field of Search .................... 604/28, 35, 96–104, 604/8, 9, 53; 606/192–194, 200

(56) References Cited

U.S. PATENT DOCUMENTS

| | | |
|---|---|---|
| 3,991,767 | 11/1976 | Miller et al. .......................... 604/8 |
| 3,995,617 | 12/1976 | Watkins et al. ..................... 128/1 D |
| 3,996,938 | 12/1976 | Clark, III ............................. 128/348 |
| 4,192,302 | 3/1980 | Boddie ............................. 128/214 R |
| 4,423,725 | 1/1984 | Baran et al. ......................... 128/207 |
| 4,494,531 | 1/1985 | Gianturco ............................ 128/1 R |
| 4,592,340 | 6/1986 | Boyles .................................... 128/1 |
| 4,705,507 | 11/1987 | Boyles .................................. 604/101 |
| 4,723,549 | 2/1988 | Wholey et al. ..................... 128/344 |
| 4,793,348 | 12/1988 | Palmaz ................................ 128/325 |
| 4,795,427 | 1/1989 | Helzel .................................. 604/53 |
| 4,817,600 | 4/1989 | Herms et al. ....................... 128/303 |
| 4,873,978 | 10/1989 | Ginsburg ............................. 128/345 |

(List continued on next page.)

FOREIGN PATENT DOCUMENTS

| | | |
|---|---|---|
| 35 35 641 A1 | 9/1987 | (DE) . |
| 43 24 637 A1 | 9/1995 | (DE) . |
| WO 97/17100 | 5/1997 | (WO) ........................... A61M/29/00 |
| WO 97/42879 | 11/1997 | (WO) ........................... A61B/17/00 |
| WO 98/02084 | 1/1998 | (WO) . |
| WO 98/24377 | 6/1998 | (WO) ........................... A61B/17/22 |

OTHER PUBLICATIONS

Barbut et al., "Determination or Size of Aortic Emboli and Embolic Load During Coronary Artery Bypass Grafting," *Ann Thorac Surg*; 63:1262–7 (1997).

(List continued on next page.)

*Primary Examiner*—Gary Jackson
(74) *Attorney, Agent, or Firm*—Fulwider Patton Lee & Utecht, LLP

(57) ABSTRACT

A perfusion shunt apparatus and methods are described for isolating and selectively perfusing a segment of a patient's cardiovascular system and for directly circulatory flow around the isolated segment. An aortic perfusion shunt apparatus is configured for deployment within a patient's aortic arch and methods are described for isolating the aortic arch vessels from the aortic lumen, for selectively perfusing the arch vessels with a fluid and for directly blood flow within the aortic lumen through a shunt past the isolated arch vessels. The perfusion shunt apparatus may be mounted on a catheter or cannula for percutaneous introduction or for direct insertion into a circulatory vessel, such as the aorta. The perfusion shunt apparatus has application for protecting a patient from embolic stroke or hypoperfusion during cardiopulmonary bypass or cardiac surgery and also for selectively perfusing the cerebrovascular circulation with oxygenated blood or with neuroprotective fluids in the presence of risk factors, such as head trauma or cardiac insufficiency. The perfusion shunt apparatus will also find application for selective perfusion of other organ systems within the body.

58 Claims, 14 Drawing Sheets

U.S. PATENT DOCUMENTS

| | | | |
|---|---|---|---|
| 4,926,858 | 5/1990 | Gifford et al. | 606/159 |
| 4,950,226 | 8/1990 | Barron | 604/8 |
| 4,969,891 | 11/1990 | Gewertz | 606/200 |
| 5,059,205 | 10/1991 | El-Nounou et al. | 606/200 |
| 5,090,960 | 2/1992 | Don Michael | 604/101 |
| 5,108,418 | 4/1992 | Lefebvre | 606/200 |
| 5,108,419 | 4/1992 | Reger et al. | 606/200 |
| 5,129,883 | 7/1992 | Black | 604/101 |
| 5,135,474 | 8/1992 | Swan | 604/8 |
| 5,152,777 | 10/1992 | Goldberg et al. | 606/200 |
| 5,163,905 | 11/1992 | Don Michael | 604/101 |
| 5,167,628 | 12/1992 | Boyles | 604/101 |
| 5,176,638 | 1/1993 | Don Michael | 604/101 |
| 5,195,955 | 3/1993 | Don Michael | 604/102 |
| 5,222,941 | 6/1993 | Don Michael | 604/101 |
| 5,306,249 | 4/1994 | Don Michael | 604/101 |
| 5,324,304 | 6/1994 | Rasmussen | 606/200 |
| 5,342,306 | 8/1994 | Don Michael | 604/101 |
| 5,375,612 | 12/1994 | Cottenceau et al. | 128/899 |
| 5,380,284 | 1/1995 | Don Michel | 601/101 |
| 5,415,630 | 5/1995 | Gory et al. | 604/53 |
| 5,460,610 | 10/1995 | Don Michael | 604/101 |
| 5,496,277 | 3/1996 | Termin et al. | 604/104 |
| 5,505,701 | 4/1996 | De Lomana | 604/99 |
| 5,549,626 | 8/1996 | Miller et al. | 606/200 |
| 5,558,642 | 9/1996 | Schweich et al. | 604/96 |
| 5,613,948 | 3/1997 | Avellanet | 604/96 |
| 5,662,671 | 9/1997 | Barbut et al. | 606/170 |
| 5,674,198 | 10/1997 | Leone | 604/101 |
| 5,695,504 | 12/1997 | Gifford et al. | 606/153 |
| 5,716,340 | 2/1998 | Schweich et al. | 604/101 |
| 5,769,816 | 6/1998 | Barbut et al. | 604/96 |
| 5,769,870 | 6/1998 | Salahieh et al. | 606/198 |
| 5,797,933 | 6/1998 | Snow et al. | 606/151 |
| 5,817,113 | 10/1998 | Gifford et al. | 606/153 |
| 5,846,260 | 12/1998 | Maahs | 606/200 |
| 5,893,841 | 3/1999 | Glickman | 604/101 |
| 5,904,697 | 5/1999 | Gifford et al. | 606/155 |

OTHER PUBLICATIONS

Barbut et al., "Aortic Atheromatosis and Risks of Cerebral Embolization," *J. Card & Vasc Anesth*; vol. 10, No. 1,: pp 24–30 (1996).

Barbut et al., "Aortic Atheroma is Related to Outcome but not Numbers of Emboli During Coronary Bypass," *Ann Thorac Surg*; 64:454–9 (1997).

Roach et al., "Adverse Cerebral Outcomes After Coronary Artery Bypass Surgery," *N Engl J Med*, vol. 335, No. 25; pp. 1857–1863 (1996).

Aberg, "Signs of Brain Cell Injury During Open Heart Operations: Past and Present," *Ann Thorac Surg*; 59:1312–5 (1995).

Murkin, "The Role of CPB Management in Neurobehavioral Outcomes After Cardiac Surgery," *Ann Thorac Surg*; 59:1308–11 (1995).

Mills, "Risk Factors for Cerebral Injury and Cardiac Surgery," *Ann Thorac Surg* 1995, 59:1296–9.

Moody et al., "Brian Microemboli Associated with Cardiopulmonary Bypass: A Histologic and Magnetic Resonance Imaging Study," *Ann Thorac Surg*; 59:1304–7 (1995).

Murkin et al., "Statement of Consensus on Assessment of Neurobehavioral Outcomes After Cardiac Surgery," *Ann Thorac Surg*; 59:1289–95 (1995).

Sherman et al., "Heart–Brain Interactions: Neurocardiology Comes of Age," *Mayo Clin Proc*; 62:1158–1160 (1987).

van der Linden, "Cerebral Hemodynamics After Low–Flow Versus No–Flow Procedures," *Ann Thorac Surg*; 59:1321–5 (1995).

Newman et al., "Predictors of Cognitive Decline After Cardiac Operation," *Ann Thorac Surg*; 59:1326–30 (1995).

Venn et al., "Cardiopulmonary Bypass: Perioperative Cerebral Blood Flow and Postoperative Cognitive Deficit," *Ann Thorac Surg*; 59:1331–5 (1995).

Blauth, "Macroemboli and Microemboli During Cardiopulmonary Bypass," *Ann Thorac Surg*; 59:1300–3 (1995).

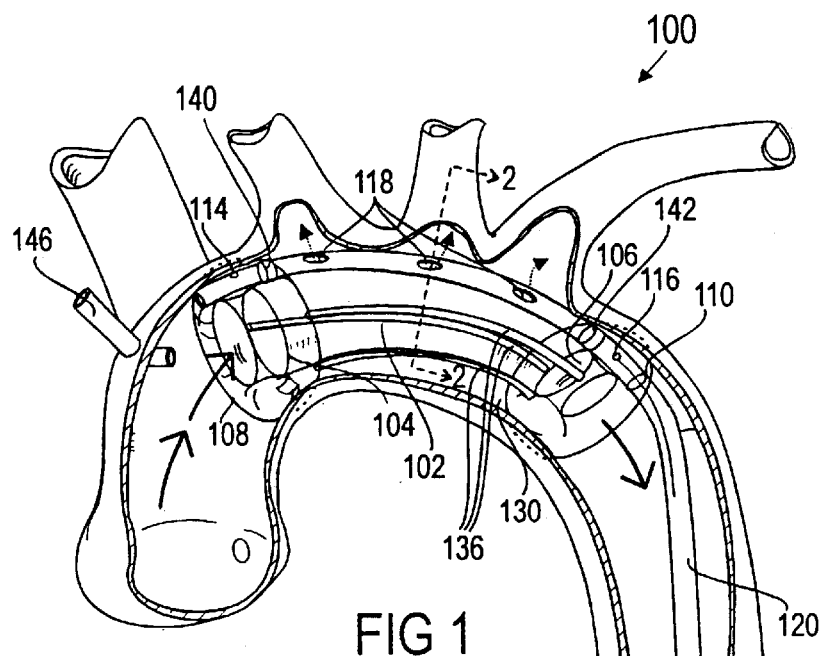
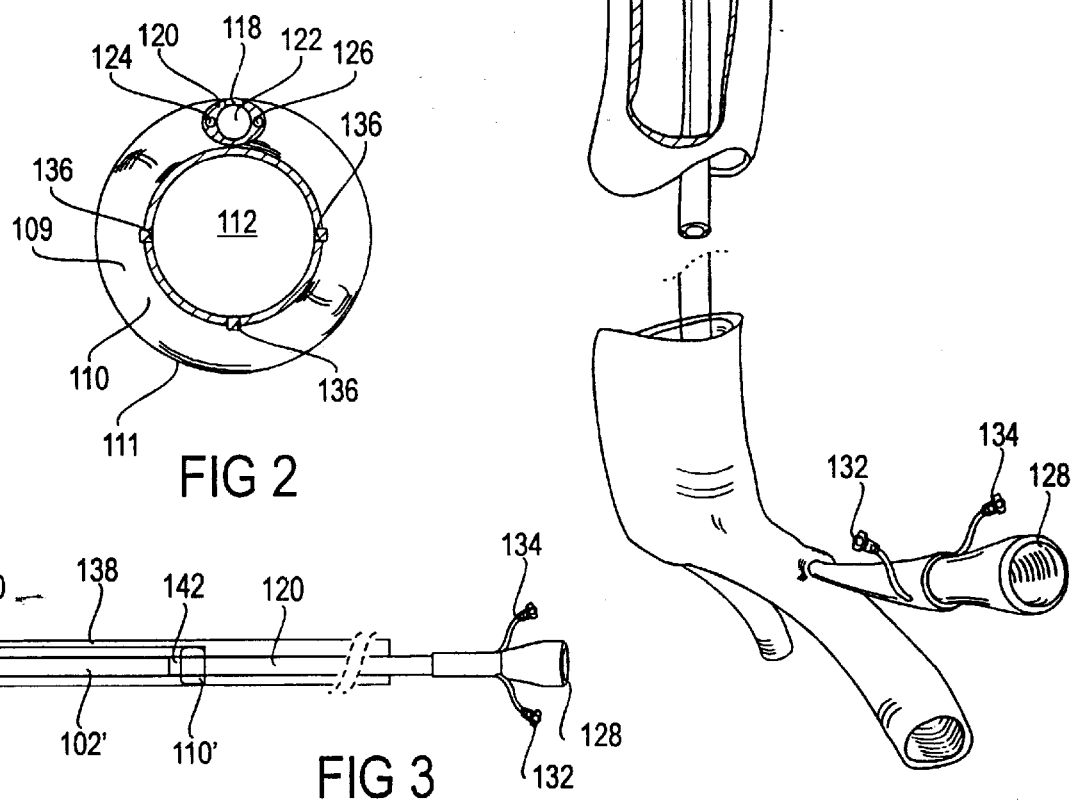
FIG 1
FIG 2
FIG 3

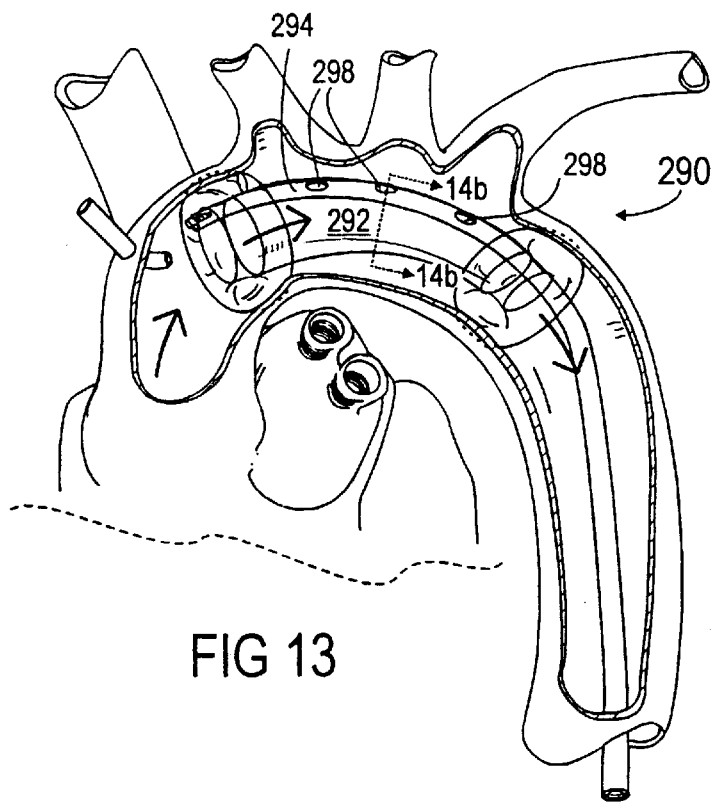
FIG 13
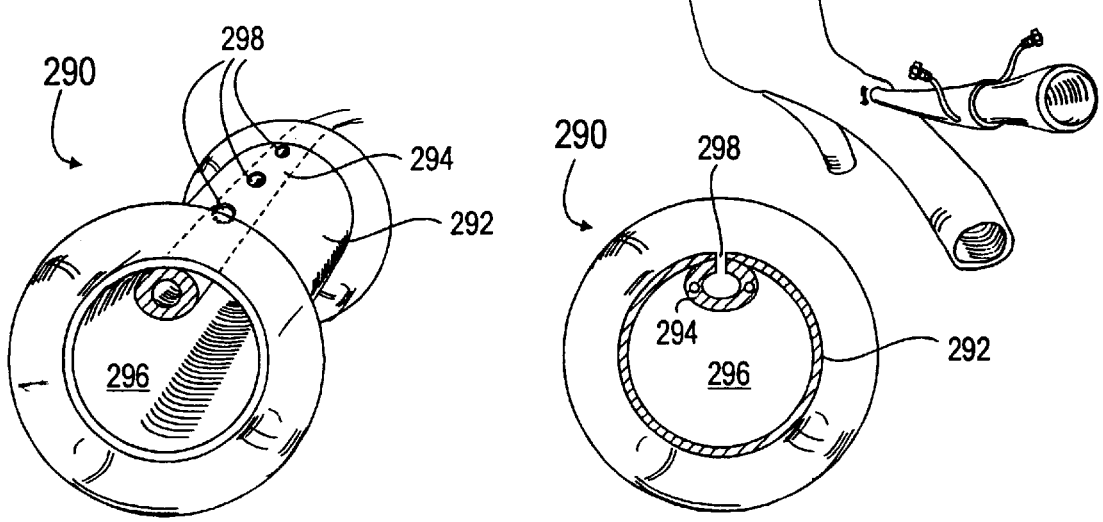
FIG 14aFIG 14b

PERFUSION SHUNT APPARATUS AND METHOD

CROSS REFERENCE TO OTHER APPLICATIONS

This application is a continuation of application Ser. No. 09/212,580, filed Dec. 14, 1998, which claims the benefit of U.S. Provisional application Ser. No. 60/069,470, filed Dec. 15, 1997, which is hereby incorporated by reference in its entirety.

FIELD OF THE INVENTION

The present invention relates generally to a perfusion shunt apparatus and to methods for isolating and selectively perfusing a segment of a patient's cardiovascular system and for directing circulatory flow around the isolated segment. More particularly, it relates to a perfusion shunt apparatus configured for deployment within a patient's aortic arch and to methods for isolating the aortic arch vessels from the aortic lumen, for selectively perfusing the arch vessels with a fluid and for directing blood flow within the aortic lumen through a shunt past the isolated arch vessels.

The perfusion shunt apparatus of the present invention may be mounted on a catheter or cannula for percutaneous introduction or for direct insertion into a circulatory vessel, such as the aorta. The perfusion shunt apparatus has application for protecting a patient from embolic stroke or hypoperfusion during cardiopulmonary bypass or cardiac surgery and also for selectively perfusing the cerebrovascular circulation with oxygenated blood or with neuroprotective fluids in the presence of risk factors, such as head trauma or cardiac insufficiency. The perfusion shunt apparatus will also find application for selective perfusion of other organ systems within the body.

BACKGROUND OF THE INVENTION

Over the past decades tremendous advances have been made in the area of heart surgery, including such life saving surgical procedures as coronary artery bypass grafting (CABG) and cardiac valve repair or replacement surgery. Cardiopulmonary bypass (CPB) is an important enabling technology that has helped to make these advances possible. Recently, however, there has been a growing awareness within the medical community and among the patient population of the potential sequelae or adverse affects of heart surgery and of cardiopulmonary bypass. Chief among these concerns is the potential for stroke or neurologic deficit associated with heart surgery and with cardiopulmonary bypass. One of the likely causes of stroke and of neurologic deficit is the release of emboli into the blood stream during heart surgery. Potential embolic materials include atherosclerotic plaques or calcific plaques from within the ascending aorta or cardiac valves and thrombus or clots from within the chambers of the heart. These potential emboli may be dislodged during surgical manipulation of the heart and the ascending aorta or due to high velocity jetting (sometimes called the "sandblasting effect") from the aortic perfusion cannula. Air that enters the heart chambers or the blood stream during surgery through open incisions or through the aortic perfusion cannula is another source of potential emboli. Emboli that lodge in the brain may cause a stroke or other neurologic deficit. Clinical studies have shown a correlation between the number and size of emboli passing through the carotid arteries and the frequency and severity of neurologic damage. At least one study has found that frank strokes seem to be associated with macroemboli larger than approximately 100 micrometers in size, whereas more subtle neurologic deficits seem to be associated with multiple microemboli smaller than approximately 100 micrometers in size. In order to improve the outcome of cardiac surgery and to avoid adverse neurological effects it would be very beneficial to eliminate or reduce the potential of such cerebral embolic events.

Several medical journal articles have been published relating to cerebral embolization and adverse cerebral outcomes associated with cardiac surgery, e.g.: Determination or Size of Aortic Emboli and Embolic Load During Coronary Artery Bypass Grafting; Barbut et al.; Ann Thorac Surg 1997; 63; 1262–7; Aortic Atheromatosis and Risks of Cerebral Embolization; Barbut et al.; J Card & Vasc Anesth, Vol 10, No 1, 1996; pp 24–30; Aortic Atheroma is Related to Outcome but not Numbers of Emboli During Coronary Bypass; Barbut et al.; Ann Thorac Surg 1997; 64; 454–9; Adverse Cerebral Outcomes After Coronary Artery Bypass Surgery; Roach et al.; New England J of Med, Vol 335, No 25, 1996; pp 1857–1863; Signs of Brain Cell Injury During Open Heart Operations; Past and Present; Åberg; Ann Thorac Surg 1995; 59; 1312–5; The Role of CPB Management in Neurobehavioral Outcomes After Cardiac Surgery; Murkin; Ann Thorac Surg 1995; 59; 1308–11; Risk Factors for Cerebral Injury and Cardiac Surgery; Mills; Ann Thorac Surg 1995; 59; 1296–9; Brain Microemboli Associated with Cardiopulmonary Bypass; A Histologic and Magnetic Resonance Imaging Study; Moody et al.; Ann Thorac Surg 1995; 59; 1304–7; CNS Dysfunction After Cardiac Surgery; Defining the Problem; Murkin; Ann Thorac Surg 1995; 59; 1287+; Statement of Consensus on Assessment of Neurobehavioral Outcomes After Cardiac Surgery; Murkin et al.; Ann Thorac Surg 1995; 59; 1289–95; Heart-Brain Interactions; Neurocardiology Comes of Age; Sherman et al.; Mayo Clin Proc 62: 1158–1160, 1987; Cerebral Hemodynamics After Low-Flow Versus No-Flow Procedures; van der Linden; Ann Thorac Surg 1995; 59; 1321–5; Predictors of Cognitive Decline After Cardiac Operation; Newman et al.; Ann Thorac Surg 1995; 59; 1326–30; Cardiopulmonary Bypass; Perioperative Cerebral Blood Flow and Postoperative Cognitive Deficit; Venn et al.; Ann Thorac Surg 1995; 59; 1331–5; Long-Term Neurologic Outcome After Cardiac Operations; Sotaniemi; Ann Thorac Surg 1995; 59; 1336–9; Macroemboli and Microemboli During Cardiopulmonary Bypass; Blauth; Ann Thorac Surg 1995; 59; 1300–3.

Commonly owned, co-pending U.S. provision application 60/060,117, and corresponding U.S. patent application 09/158,405, which are hereby incorporated by reference, describe an aortic perfusion filter catheter for prevention of cerebral embolization and embolic stroke during cardiopulmonary bypass or cardiac surgery. The patent literature also includes several other references relating to vascular filter devices for reducing or eliminating the potential of embolization. These and all other patents and patent applications referred to herein are hereby incorporated by reference in their entirety. The following U.S. patents relates to vena cava filters; U.S. Pat. Nos. 5,549,626, 5,415,630, 5,152,777, 5,375,612, 4,793,348, 4,817,600, 4,969,891, 5,059,205, 5,324,304, 5,108,418, 4,494,531. The following U.S. patents relate to vascular filter devices: 5,496,277, 5,108,419, 4,723, 549, 3,996,938. The following U.S. patents relate to aortic filters or aortic filters associated with atherectomy devices: U.S. Pat. Nos. 5,662,671, 5,769,816. The following international patent applications relate to aortic filters or aortic filters associated with atherectomy devices: WO 97/17100, WO 97/42879, WO 98/02084. The following international patent application relates to a carotid artery filter; WO 98/24377. The patent literature also includes the following U.S. patents related to vascular shunts and associated catheters: U.S. Pat. Nos. 3,991,767, 5,129,883, 5,613,948. None of these patents related to vascular shunts provides an apparatus or method suitable for preventing of cerebral embolization and embolic stroke or for performing selective perfusion of the aortic arch vessels to prevent hypoperfusion during cardiopulmonary bypass or cardiac surgery.

While some of these previous devices and systems represent advances in the prevention of some causes of neurologic damage, there continues to be a tremendous need for improved apparatus and methods to prevent cerebral embolization, embolic stroke and cerebral hypoperfusion during cardiopulmonary bypass and cardiac surgery. Similarly, there continues to be a tremendous need for apparatus and methods for selective perfusion of the cerebrovascular circulation with oxygenated blood or with neuroprotective fluids in the presence of risk factors, such as head trauma or cardiac insufficiency and also for selective perfusion of other organ systems within the body.

SUMMARY OF THE INVENTION

In keeping with the foregoing discussion, the present invention takes the form of a perfusion shunt apparatus and methods for isolating and selectively perfusing a segment of a patient's cardiovascular system and for directing circulatory flow around the isolated segment. In a particularly preferred embodiment of the invention, the perfusion shunt apparatus is configured as an aortic perfusion shunt apparatus for deployment within a patient's aortic arch and methods are described for isolating the aortic arch vessels from the aortic lumen, for selectively perfusing the arch vessels with a fluid and for directing blood flow within the aortic lumen through a shunt conduit past the isolated arch vessels. The perfusion shunt apparatus may be mounted on a catheter or cannula for percutaneous introduction via peripheral artery access or for direct insertion into a circulatory vessel, such as the aorta. The perfusion shunt apparatus protects the patient from cerebral embolization and embolic stroke during cardiopulmonary bypass or cardiac surgery by directing potential embolic downstream from the aortic arch vessels where they will be better tolerated by the body. The perfusion shunt apparatus further protects the patient from cerebral hypoperfusion by providing selective perfusion of the aortic arch vessels and the cerebrovascular circulation with oxygenated blood or with neuroprotective fluids. The perfusion shunt apparatus also finds application for selective perfusion of the cerebrovascular circulation in the presence of risk factors, such as head trauma or cardiac insufficiency. The perfusion shunt apparatus will also find application for selective perfusion of other organ systems within the body.

The perfusion shunt apparatus of the present invention includes an expandable shunt conduit with an upstream end, a downstream end and an internal lumen. The expandable shunt conduit is mounted on a catheter or cannula for percutaneous introduction via peripheral artery access or for direct insertion into the aorta. The expandable shunt conduit is a generally cylindrical tube of a flexible polymeric material or fabric that may be impermeable or porous to blood. Located at the upstream end of the expandable shunt conduit is an upstream sealing member. A downstream sealing member is located at the downstream end of the expandable shunt conduit. Optionally, the expandable shunt conduit may also include a plurality of support members that bridge between the upstream sealing member and the downstream sealing member. When deployed, the upstream sealing member and the downstream sealing member support the expandable shunt conduit in an open, deployed configuration and create a seal between the expandable shunt conduit and the vessel wall. An annular chamber is created between the vessel wall and the shunt conduit. A perfusion lumen within the catheter shaft communicates with the annular chamber external to the shunt conduit.

In one particularly preferred embodiment, the upstream sealing member and the downstream sealing member are inflatable toroidal balloon cuffs, which are sealingly attached to the upstream end and the downstream end of the expandable shunt conduit. In another embodiment, the upstream sealing member and the downstream sealing member are in the form of selectively deployable external flow valves. In yet another embodiment, the upstream sealing member and the downstream sealing member include extendible and retractable elongated expansion members to expand the upstream and downstream ends of the expandable shunt conduit until they contact and create a seal against the inner surface of the aorta.

Optionally, an outer tube may be provided to cover the shunt conduit when it is in the collapsed state in order to create a smooth outer surface for insertion and withdrawal of the perfusion shunt apparatus and to prevent premature deployment of the shunt conduit. Optionally, each embodiment of the perfusion shunt apparatus may also include an occlusion device, such as an inflatable balloon, to selectively occlude and seal the lumen of the expandable shunt conduit. Each embodiment of the perfusion shunt apparatus may also include an embolic filter for filtering potential emboli from the blood passing through the internal lumen of the expandable shunt conduit. Each embodiment of the perfusion shunt apparatus may include one or more radiopaque markers, sonoreflective markers or light emitting devices to enhance imaging of the apparatus using fluoroscopy, ultrasonic imaging or aortic transillumination.

BRIEF DESCRIPTION OF THE DRAWINGS

FIGS. 1–3 show a perfusion shunt apparatus according to the present invention configured for retrograde deployment in a patient's aortic arch via a peripheral arterial access point. FIG. 1 is a cutaway perspective view of the perfusion shunt apparatus deployed within the aortic arch via femoral artery access. FIG. 2 is a cross section of the perfusion shunt apparatus taken along line 2—2 in FIG. 1. FIG. 3 shows the apparatus with the shunt in a collapsed state for insertion or withdrawal of the device from the patient.

FIG. 5 is a cutaway perspective view of the perfusion shunt apparatus deployed within the aorta. FIG. 6 shows the apparatus with the perfusion shunt conduit in a collapsed state for insertion or withdrawal of the device from the patient.

FIG. 7 is a cutaway perspective view of the perfusion shunt apparatus deployed within the aorta. FIG. 8 shows the apparatus with the perfusion shunt in a collapsed state for insertion or withdrawal of the device from the aorta.

FIG. 13 shows an alternate construction of an aortic perfusion shunt apparatus according to the present invention.

FIG. 14a is an end view of the aortic perfusion shunt apparatus of FIG. 13. FIG. 14b is a cross section of the aortic perfusion shunt apparatus of FIG. 13.

FIG. 20 is a cutaway perspective view of the perfusion shunt apparatus deployed within the aorta. FIG. 21 shows the apparatus with the perfusion shunt conduit in a collapsed state for insertion or withdrawal of the device from the patient.

DETAILED DESCRIPTION OF THE INVENTION

Figure 4:
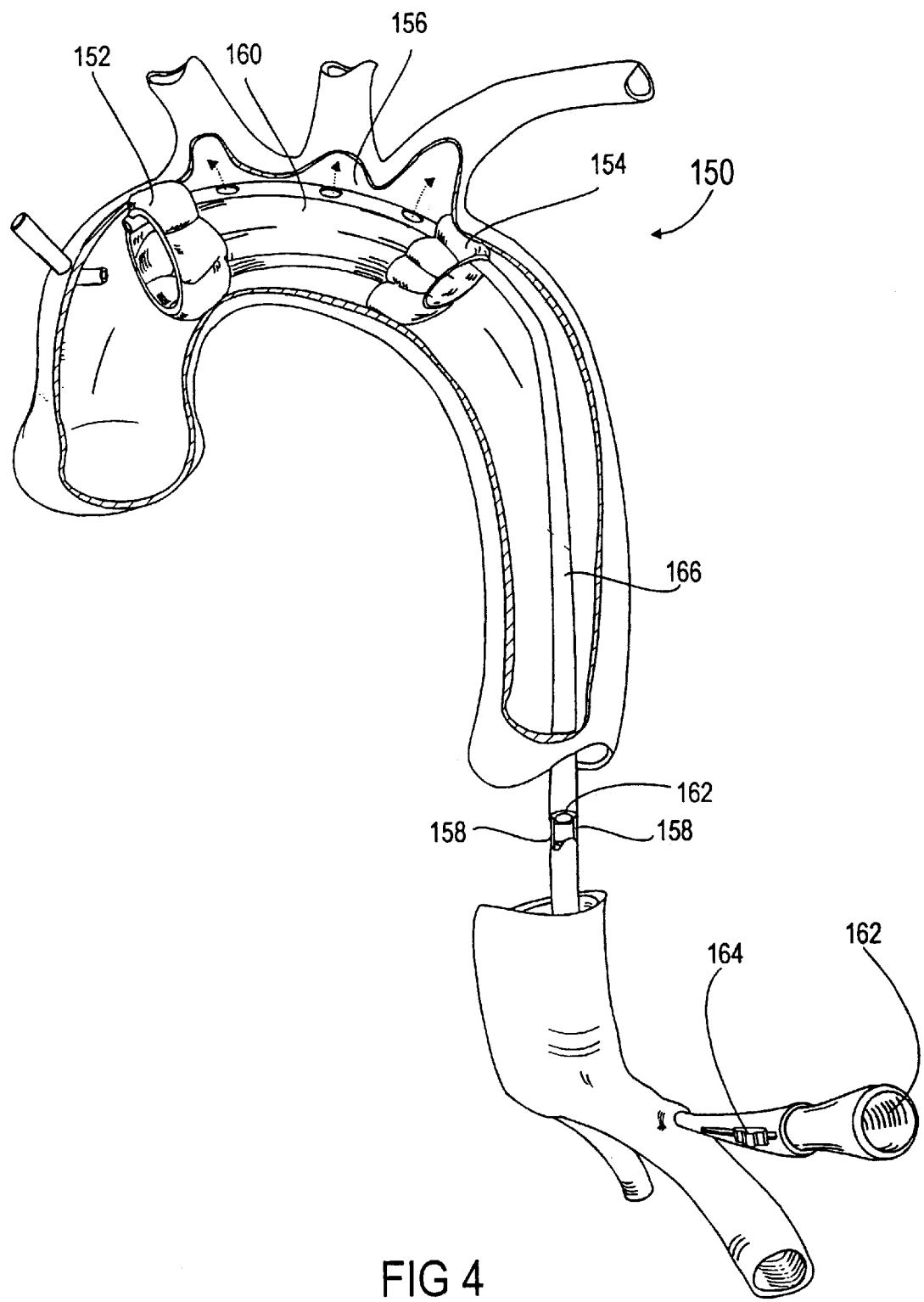
FIG. 4 shows an alternate embodiment of the perfusion shunt apparatus using external flow control valves as sealing members.

FIGS. 1–3 show a perfusion shunt apparatus 100 according to the present invention configured for retrograde deployment in a patient's aortic arch via a peripheral arterial access point. FIG. 1 is a cutaway perspective view of the perfusion shunt apparatus 100 deployed within the aortic arch via femoral artery access. FIG. 2 is a cross section of the perfusion shunt apparatus 100 taken along line 2—2 in FIG. 1. FIG. 3 shows the distal end of the apparatus with the shunt conduit 102 in a collapsed state for insertion or withdrawal of the device from the patient.

Referring now to FIG. 1, the perfusion shunt apparatus 100 is shown in an expanded or deployed state within a patient's aortic arch. The perfusion shunt apparatus 100 includes an expandable shunt conduit 102, which has an upstream end 104, a downstream end 106 and an internal lumen 112. Preferably, the expandable shunt conduit 102 is constructed as a generally cylindrical tube of a flexible polymeric material or fabric that is substantially impermeable to blood or fluid flow. Suitable materials for the expandable shunt conduit 102 include, but are not limited to, polyvinylchloride, polyurethane, polyethylene, polypropylene, polyamides (nylons), polyesters and alloys of copolymers thereof, as well as knitted, woven or nonwoven fabrics. Located at the upstream end 104 of the expandable shunt conduit 102 is an upstream shunt conduit support and sealing member 108. A downstream shunt conduit support and sealing member 110 is located at the downstream end 106 of the expandable shunt conduit 102. When deployed, the upstream sealing member 108 and the downstream sealing member 110 support the expandable shunt conduit 102 in an open, deployed configuration and create a seal between the expandable shunt conduit 102 and the vessel wall, as shown in FIG. 1. An annular chamber 130 is thus created between the vessel wall and the shunt conduit 102. The annular chamber 130 is delimited on the upstream end by the upstream sealing member 108 and on the downstream end by the downstream sealing member 110 and is isolated from the internal lumen 112 by the cylindrical wall of the shunt conduit 102. In one particularly preferred embodiment, the upstream shunt conduit support and sealing member 108 and the downstream shunt conduit support and sealing member 110 are configured as inflatable annular balloon cuffs, which are sealingly attached to the upstream end 104 and the downstream end 106 of the expandable shunt conduit 102, respectively. Suitable materials for the inflatable annular balloon cuffs 108, 110 include flexible polymers and elastomers, which include, but are not limited to, polyvinylchloride, polyurethane, polyethylene, polypropylene, polyamides (nylons), polyesters, latex, silicone, and alloys, copolymers and reinforced composites thereof.

Optionally, the expandable shunt conduit 102 may also include a plurality of support members 136, which bridge between the upstream sealing member 108 and the downstream sealing member 110. The support members 136 strengthen the expandable shunt conduit 102 and help to hold the internal lumen 112 open when the perfusion shunt apparatus 100 is deployed. The support members 136 may be made of a semi-rigid, resilient wire or polymer material joined to or formed integrally with the wall of the shunt conduit 102. The support members 136 may be longitudinally oriented with respect to the shunt conduit 102, as shown, or they may be configured as one or more circumferential hoops or helical support members. The expandable shunt conduit 102 and the support members 136 may be made in a straight, but somewhat flexible, configuration so that they conform naturally to the internal curvature of the patient's aortic arch when deployed. Alternatively, the expandable shunt conduit 102 and the support members 136 may be preshaped with a curve to match the internal curvature of the patient's aortic arch.

Preferably, the expandable shunt conduit 102 between the upstream member 108 and the downstream sealing member 110 will have a length sufficient to bridge across the target branch vessels without occluding them. In various embodiments configured for different clinical applications, the expandable shunt conduit 102 is preferably from 1 cm to 40 cm in length, more preferably from 5 cm to 15 cm in length. In one particularly preferred embodiment configured for perfusing the aortic arch vessels in adult human patients, the expandable shunt conduit 102 is preferably approximately 8 cm to 12 cm in length. Likewise, the diameter of the expandable shunt conduit 102 is also adaptable for a variety of different clinical applications. The expandable shunt conduit 102 should have a large enough diameter, when expanded, to allow sufficient blood flow through the expandable shunt conduit 102 to adequately perfuse the organs and tissues downstream of the deployed perfusion shunt apparatus 100. Preferably, the expandable shunt conduit 102 is of a diameter slightly smaller than the host vessel into which it is intended to be introduced so that the wall of the expandable shunt conduit 102 is separated from the vessel wall creating an annular chamber 130 between the upstream sealing member 108 and the downstream sealing member 110, as described above. This arrangement also prevents the wall of the expandable shunt conduit 102 from occluding or restricting flow of perfusate into the target branch vessels. In various embodiments configured for different clinical applications, the expandable shunt conduit 102 is preferably from 0.2 cm to 10 cm in diameter, more preferably from 1 cm to 5 cm in diameter. For deployment in the aortic arch and perfusing the aortic arch vessels in adult human patients, the expandable shunt conduit 102 is preferably approximately 1.0 cm to 2.5 cm in diameter. With these dimensions, the internal lumen 112 of the expandable shunt conduit 102 will be capable of delivering approximately 2 to 4 liters of oxygenated blood per minute from the heart, which are necessary to adequately perfuse the organs and tissues downstream of the aortic arch. When deployed, the upstream sealing member 108 and the downstream sealing member 110 preferably have an inner diameter approximately equal to the diameter of the expandable shunt conduit 102 and an outer diameter sufficient to seal against the interior wall of the host vessel. In various embodiments configured for different clinical applications, the upstream sealing member 108 and the downstream sealing member 110 preferably have an outer diameter of 0.3 cm to 15 cm, more preferably 1 cm to 7 cm. For deployment in the aortic arch in adult human patients, the upstream sealing member 108 and the downstream sealing member 110 preferably have an outer diameter of approximately 1.5 cm to 3.5 cm.

Preferably, the expandable shunt conduit 102 is mounted on an elongated catheter shaft or cannula 102 for introduction into the patient's circulatory system. In this exemplary embodiment of the perfusion shunt apparatus 100, the elongated catheter shaft 120 is configured for retrograde deployment of the expandable shunt conduit 102 in a patient's aortic arch via a peripheral arterial access point, such as the femoral artery. The elongated catheter shaft 120 should have a length sufficient to reach from the arterial access point where it is inserted into the patient to the aortic arch. For femoral artery deployment, the elongated catheter shaft 120 preferably has a length from approximately 60 to 120 cm, more preferably 70 to 90 cm. The elongated catheter shaft 120 is preferably extruded of a flexible thermoplastic material or a thermoplastic elastomer. Suitable materials for the elongated catheter shaft 120 include, but are not limited to, polyvinylchloride, polyurethane, polyethylene, polypropylene, polyamides (nylons), polyesters, and alloys or copolymers thereof, as well as braided, coiled or counterwound wire or filament reinforced composites. Optionally, the distal end of the catheter shaft 120 may be preshaped with a curve to match the internal curvature of the patient's aortic arch.

As seen in the cross section of the apparatus in FIG. 2, the elongated catheter shaft 120 has a perfusion lumen 122, a first inflation lumen 124 and a second inflation lumen 126. The catheter shaft 120 has one or more perfusion ports 118 that connect the perfusion lumen 122 with the annular chamber 130 on the exterior of the shunt conduit 102 between the upstream sealing member 108 and the downstream sealing member 110. The proximal end 128 of the elongated catheter shaft 120 is adapted for connecting the perfusion lumen 122 to a cardiopulmonary bypass pump or other source of oxygenated blood or other fluid using standard barb connectors or other connectors, such as a standard luer fitting (not shown). The perfusion lumen 122 should be configured to allow sufficient fluid flow to preserve organ and tissue function of the organs and tissues supplied by the target branch vessels. For cerebral perfusion, the perfusion lumen 122 should be configured to allow sufficient fluid flow to preserve organ function of the brain and other tissues supplied by the arch vessels. For normothermic perfusion with oxygenated blood, the perfusion lumen 122 should have sufficient cross-sectional area to allow 0.5 to 1.5 liters per minute, and more preferably 0.75 to 1.0 liters per minute, of blood flow without significant hemolysis or other damage to the blood. For hypothermic perfusion with cooled oxygenated blood, the flow rate can be reduced to 0.25 to 0.75 liters per minute, permitting a reduction in the cross-sectional area of the perfusion lumen 122. For perfusion with blood substitutes, such as perfluorocarbons, or with neuroplegic solutions, the cross-sectional area of the perfusion lumen 122 should be designed to allow sufficient flow rate to preserve organ function given the viscosity, pressure susceptibility and the oxygen and metabolite transport capabilities of the chosen perfusate fluid.

Optionally, the perfusion shunt apparatus 100 may be configured for introduction over a guidewire. For example, the perfusion lumen 122 of the elongated catheter shaft 120 may be adapted for accepting a guidewire. The perfusion lumen 122 may be provided with a distal opening at the distal end of the elongated catheter shaft 120 for passing a guidewire, such as an 0.035 or 0.038 inch diameter guidewire. Optionally, a valve, such as the catheter valve described in U.S. Pat. No. 5,085,635, which is hereby incorporated by reference, may be included at the distal end of the perfusion lumen 122 to prevent perfusate from passing through the distal opening during perfusion. Alternatively, the elongated catheter shaft 120 may include an addition lumen (not shown) for introducing the perfusion shunt apparatus 100 over a guidewire.

In various embodiments of the perfusion shunt apparatus 100 configured for different clinical applications, the elongated catheter shaft 120 preferably has an external diameter from 3 to 24 French size (1 to 8 mm diameter), more preferably from 8 to 16 French size (2.7 to 5.3 mm diameter). In one particularly preferred embodiment configured for perfusing the aortic arch vessels with normothermic blood in adult human patients, the elongated catheter shaft 120 preferably has a length of approximately 70 to 90 cm and an external diameter from approximately 10 to 14 French size (3.3 to 4.6 mm diameter), which allows a flow rate of approximately 0.75 to 1.0 liters per minute. In another preferred embodiment configured for perfusing the aortic arch vessels with hypothermic blood in adult human patients, the elongated catheter shaft 120 preferably has a length of approximately 70 to 90 cm and an external diameter from approximately 8 to 12 French size (2.6 to 4.0 mm diameter), which allows a flow rate of approximately 0.25 to 0.75 liters per minute.

Preferably, the perfusion shunt apparatus 100 includes one or more markers, which may include radiopaque markers and/or sonoreflective markers, to enhance imaging of the perfusion shunt apparatus 100 using fluoroscopy or ultrasound, such as transesophageal echography (TEE). By way of example, FIGS. 1 and 3 show a perfusion shunt apparatus 100 having a first, upstream radiopaque and/or sonoreflective marker ring 140 on the catheter shaft 120 just proximal to the upstream sealing member 108 and a second, downstream radiopaque and/or sonoreflective marker ring 142 on the catheter shaft 120 just distal to the downstream sealing member 110. Alternatively or additionally, radiopaque markers and/or sonoreflective markers may be placed on the sealing members 108, 110 and/or the shunt conduit 102 to show the position and/or the deployment state of the perfusion shunt apparatus 100.

A first inflation port 114 connects the first inflation lumen 124 with the interior of the inflatable annular balloon cuff that forms the upstream sealing member 108. The proximal end of the first inflation lumen 124 is connected to a first luer fitting 132 or other suitable inflation connector. A second inflation port 114 connects the second inflation lumen 126 with the interior of the inflatable annular balloon cuff of the downstream sealing member 110. The proximal end of the second inflation lumen 126 is connected to a second luer fitting 134 or other suitable inflation connector. This configuration allows individual inflation and deflation control of the upstream sealing member 108 and the downstream sealing member 110. In an alternate configuration of the perfusion shunt apparatus 100, the elongated catheter shaft 120 may be made with a single inflation lumen connected to both the first inflation port 114 and the second inflation port 114 and connected at the proximal end to a single luer fitting. In this alternate configuration, the upstream sealing member 108 and the downstream sealing member 110 would be simultaneously inflated and deflated through the single inflation lumen. Such a configuration could be used to reduce the overall diameter of the elongated catheter shaft 120.

Referring now to FIG. 3, the perfusion shunt apparatus 100 is shown in an undeployed or collapsed state for insertion or withdrawal of the device from the patient. To place the perfusion shunt apparatus 100 in the collapsed state, the upstream sealing member 108 and the downstream sealing member 110' are deflated and the shunt conduit 102' is wrapped or folded around the catheter shaft 120 to reduce its overall diameter. Optionally, an outer tube 138 may be provided to cover the shunt conduit 102 when it is in the collapsed state in order to create a smooth outer surface for insertion and withdrawal of the perfusion shunt apparatus 100 and to prevent premature deployment of the shunt conduit 102.

The perfusion shunt apparatus 100 is prepared for use by folding or compressing the shunt conduit 102' into a collapsed state within the outer tube 138, as shown in FIG. 3. The distal end of the perfusion shunt apparatus 100 is then inserted into the aorta in a retrograde fashion. Preferably, this is done through a peripheral arterial access, such as the femoral artery or subclavian artery, using the Seldinger technique or an arterial cutdown. Alternatively, the perfusion shunt apparatus 100 may be introduced directly through an incision into the descending aorta after the aorta has been surgically exposed. The perfusion shunt apparatus 100 is advanced up the descending aorta and across the aortic arch while in the collapsed state. The position of the perfusion shunt apparatus 100 may be monitored using fluoroscopy or ultrasound, such as transesophageal echography (TEE), with the help of the radiopaque markers and/or sonoreflective markers 140, 142 on the catheter shaft 120. When the upstream marker ring 140 is positioned in the ascending aorta between the aortic valve and the brachiocephalic artery and the downstream marker ring 142 is positioned downstream of the left subclavian artery, the outer tube 124 is withdrawn and the shunt conduit 102 is expanded by inflating the upstream sealing member 108 and the downstream sealing member 110, as shown in FIG. 1. To encourage the upstream sealing member 108 and the downstream sealing member 110 to seal with the inner surface of the aorta, they may be made with differential wall compliance that encourages the toroidal balloons to expand outward, away from the expandable shunt conduit 102. For example, the upstream sealing member 108 and the downstream sealing member 110 may be made with a thicker balloon wall 109 near the inner surface of the toroidal balloon and a thinner balloon wall 111 near the outer surface of the toroidal balloon, as indicated in FIG. 2. Differential wall compliance can also be accomplished by combining different balloon materials of varying elasticity. The annular chamber 130 surrounding the shunt conduit 102 created by inflation of the upstream sealing member 108 and the downstream sealing member 110 is fluidly connected to the arch vessels and is isolated from the lumen of the aorta. Once the perfusion shunt apparatus 100 is deployed, oxygenated blood or another chosen perfusate may be infused through the perfusion lumen 122 to selectively perfuse the arch vessels that deliver blood to the brain and the upper extremities.

If the perfusion shunt apparatus 100 is to be used in conjunction with cardiopulmonary bypass, an arterial return cannula 146 may be placed in the ascending aorta upstream of the shunt conduit 102 using known methods. Blood flow the aortic lumen from the beating heart and/or from the arterial return cannula 146 is shunted past the arch vessels through the internal lumen 112 of the shunt conduit 102. If desired, a standard cross clamp and a cardioplegia needle or an intra-aortic occlusion catheter, such as described in U.S. Pat. Nos. 5,308,320 and 5,383,854, by Peter Safar, S. William Stezoski, and Miroslav Klain, which are hereby incorporated by reference may be applied upstream of the arterial cannula 146 for isolating the coronary arteries and inducing cardioplegic arrest. After use, the shunt conduit 102 is returned to the collapsed position by deflating the upstream sealing member 108 and the downstream sealing member 110 and advancing the outer tube 138 distally over the shunt conduit 102, then the apparatus 100 is withdrawn from the patient.

Selective perfusion of the arch vessels provides protection from embolization or hypoperfusion of the brain. Any potential emboli from the cardiopulmonary bypass circuit or from surgical manipulation of the heart or the aorta are prevented from entering the neurovascular through the arch vessels. After use, the perfusion shunt assembly 102 is returned to the collapsed position and the catheter 100 is withdrawn from the patient.

In an alternate method for use with this and other embodiments of the perfusion shunt apparatus described herein, the perfusion shunt apparatus 100 may be deployed by inflating the upstream sealing member 108 only to expand the shunt conduit 102 and leaving the downstream sealing member 110 uninflated. Aortic blood flow from the heart or from an arterial return cannula 146 will hold the shunt conduit 102 in the open position. Potential emboli are prevented from entering the arch vessels and the cerebral circulation by pumping perfusate through the perfusion lumen 122 at a sufficient rate to create a pressure gradient that prevents blood flowing through the shunt conduit 102 from entering the annular chamber 130 surrounding the shunt conduit 102. When using this alternate method, the perfusion shunt apparatus 100 may be simplified by eliminating the downstream sealing member 110 from the shunt conduit 102.

In an alternate embodiment of the perfusion shunt apparatus 150, shown deployed within a patient's aortic arch in FIG. 4, the upstream sealing member 152 and the downstream sealing member 154 may take the form of external flow control valves, as described in commonly owned, copending patent application 08/665,635, 08/664,361, now U.S. Pat. No. 5,827,237, and 08/664,360, now U.S. Pat. No. 5,833,671, which are hereby incorporated by reference. In this alternate embodiment, the upstream sealing member 152 would preferably be in the form of an antegrade, peripheral flow valve and the downstream sealing member 154 would preferably be in the form of a retrograde, peripheral flow vale. In such a configuration, positive perfusion pressure within the annular chamber 156 surrounding the shunt conduit 160 would tend to seal the upstream sealing member 152 and the downstream sealing member 154 against the vessel wall. However, in the event that the perfusion pressure within the annular chamber 156 dropped below aortic pressure, the upstream sealing member 152 would open so that aortic blood flow could augment the cerebral blood flow delivered through the perfusion lumen 162. Alternatively or in addition to this passive valve action, the upstream sealing member 152 and the downstream sealing member 154 may be actively deployed by one or more actuation wires 158 extending through the elongated shaft 166 of apparatus. The actuation wires 158 would be attached at their distal ends to one or more of the valve leaflets of the upstream sealing member 152 and the downstream sealing member 154 and at their proximal ends to one or more slide buttons 164 or other actuation means for independent or simultaneous deployment.

The foregoing examples of the perfusion shunt apparatus of the present invention show retrograde deployment of the device within the aorta via femoral artery access. Each of the described embodiments of the perfusion shunt apparatus can also be adapted for retrograde deployment via subclavian artery access or for antegrade or retrograde deployment via direct aortic puncture.

Retrograde deployment of the perfusion shunt apparatus 100 via direct aortic puncture is quite similar to introduction via femoral artery access, except that the perfusion shunt apparatus 100 is introduced directly into the descending aorta after it has been surgically exposed, for example during open-chest or minimally invasive cardiac surgery. Because of the direct aortic insertion, the length and the diameter of the catheter shaft 120 may be significantly reduced.

Figure 5:
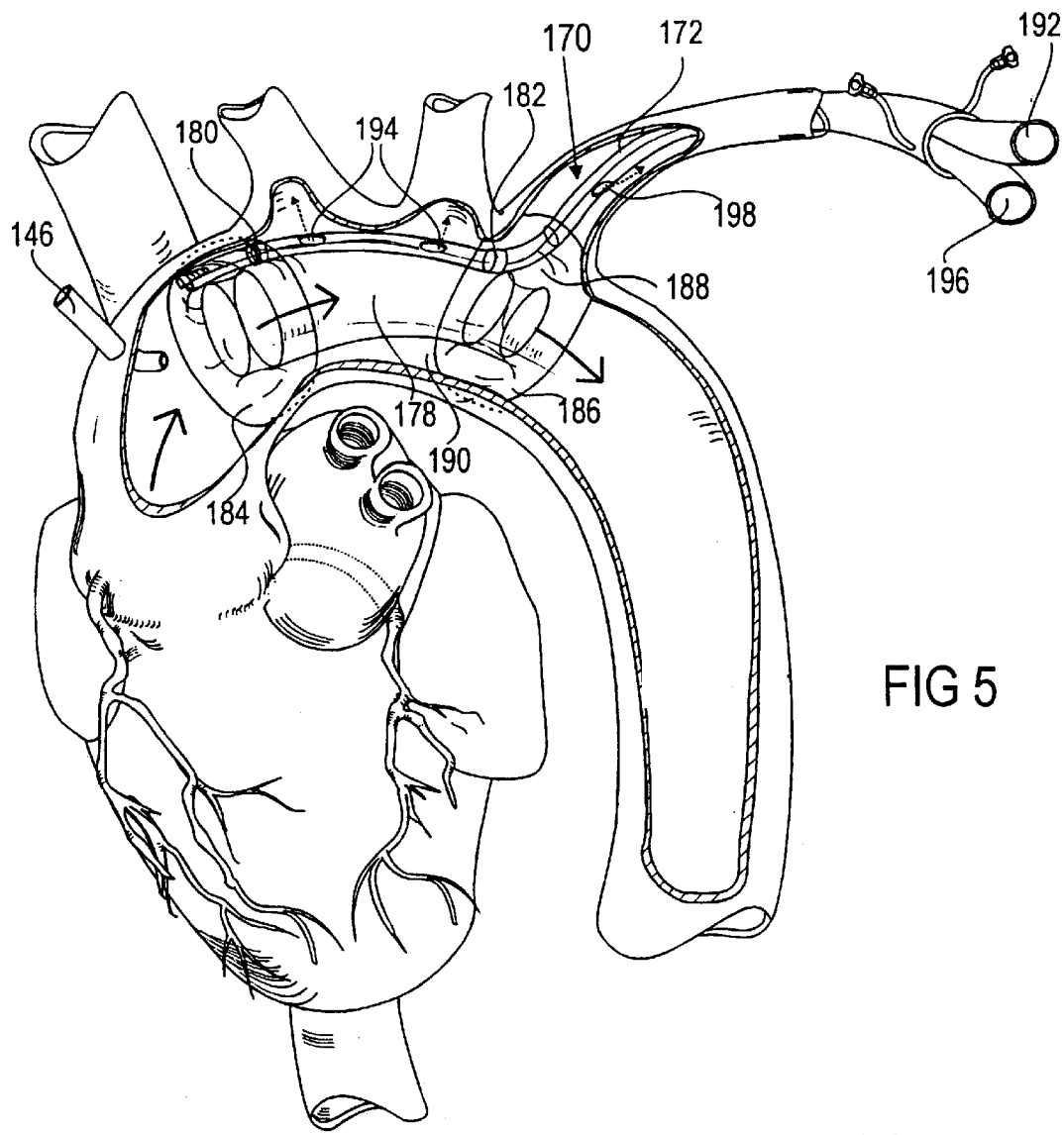
FIGS. 5 and 6 show an aortic perfusion shunt apparatus configured for retrograde deployment via subclavian artery access.
Figure 6:
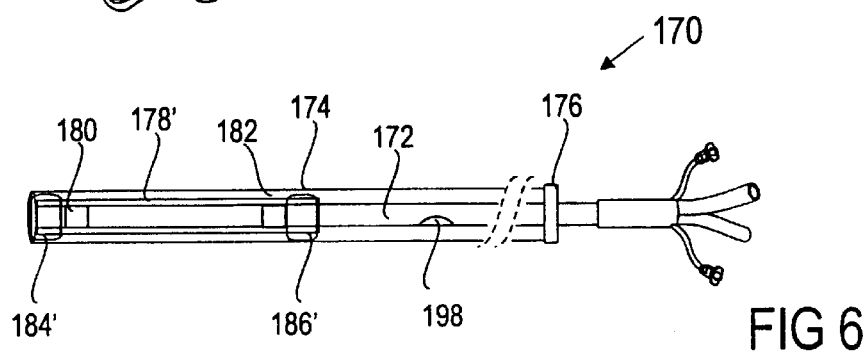

FIGS. 5 and 6 show an aortic perfusion shunt apparatus 170 configured for retrograde deployment via subclavian artery access. FIG. 5 is a cutaway perspective view of the perfusion shunt apparatus 170 deployed within the aorta. FIG. 6 shows the distal end of the apparatus 170 with the perfusion shunt in a collapsed state for insertion or withdrawal of the device from the patient. Because it is intended for subclavian artery access, the perfusion shunt apparatus 170 has a catheter shaft 172 with a length of approximately 45 to 90 cm. Because of the shorter length, as compared to the femoral version of the catheter, the outside diameter of the catheter shaft 172 can be reduced to 6 to 12 French size (2 to 4 mm outside diameter) for delivering the 0.25 to 1.5 liters per minute of oxygenated blood needed to perfuse the arch vessels to preserve organ function. The reduced diameter of the catheter shaft 172 is especially advantageous for subclavian artery delivery of the perfusion shunt apparatus 170. To further reduce the size of the catheter system for subclavian or femoral artery delivery, the outer tube 174 may be adapted for use as an introducer sheath by the addition of an optional hemostasis valve 176 at the proximal end of the outer tube 174. This eliminates the need for a separate introducer sheath for introducing the perfusion shunt apparatus 170 into the circulatory system.

In use, the perfusion shunt apparatus 170 is introduced into the subclavian artery, using the Seldinger technique or an arterial cutdown, with the perfusion shunt conduit 178' in a collapsed state within the outer tube 176, as shown in FIG. 6. The perfusion shunt apparatus 170 is advanced across the aortic arch while in the collapsed state. The position of the perfusion shunt apparatus 170 may be monitored using fluoroscopy or ultrasound, such as transesophageal echography (TEE) with the help of upstream and downstream radiopaque markers and/or sonoreflective markers 180, 182, located on the catheter shaft 172 and/or the perfusion shunt conduit 178. When the upstream marker 180 is positioned in the ascending aorta between the aortic valve and the brachiocephalic artery and the downstream marker 182 is positioned at the ostium of the left subclavian artery, the outer tube 174 is withdrawn and the shunt conduit 102 is expanded by inflating the upstream sealing member 184 and the downstream sealing member 186, as shown in FIG. 5. In a preferred embodiment of the apparatus, the catheter shaft 172 has a preformed bend 188 at the point where it passes through the downstream sealing member 186 and where it makes the transition from the left subclavian artery into the aortic arch to assist seating the apparatus 170 in the correct position. The downstream sealing member 186 is configured so that when it is inflated it also occludes the left subclavian artery. The annular chamber 190 surrounding the shunt conduit 178 created by inflation of the upstream sealing member 184 and the downstream sealing member 186 is fluidly connected to the arch vessels and is isolated from the lumen of the aorta.

Once the perfusion shunt apparatus 170 is deployed, oxygenated blood or another chosen perfusate may be infused through a first perfusion lumen 192 and out through one or more perfusion ports 194 to selectively perfuse the arch vessels that deliver blood to the brain and the upper extremities. Because the left subclavian artery is occluded by the downstream sealing member 186 when it is inflated, a second perfusion lumen 196 is provided in the catheter shaft 172 to perfuse the left upper extremity through a perfusion port 198 located on the catheter shaft 172 proximal to the downstream sealing member 186. Additionally or alternatively, the arch vessels may be perfused through a cannula placed in a branch of one of the arch vessels, such as the patient's right subclavian artery. Such an arrangement would allow the perfusion lumen 192 to be reduced in size or even eliminated from the apparatus 170. Again, if the perfusion shunt apparatus 170 is to be used in conjunction with cardiopulmonary bypass, an arterial return cannula 146 may be placed in the ascending aorta upstream of the shunt conduit 178 using known methods. Blood flow through the aortic lumen from the beating heart and/or from the arterial return cannula 146 is shunted past the arch vessels through the internal lumen of the shunt conduit 178. After use, the shunt conduit 178 is returned to the collapsed position by deflating the upstream sealing member 184 and the downstream sealing member 186 and advancing the outer tube 176 distally over the shunt conduit 178, then the apparatus 170 is withdrawn from the patient.

Figure 7:
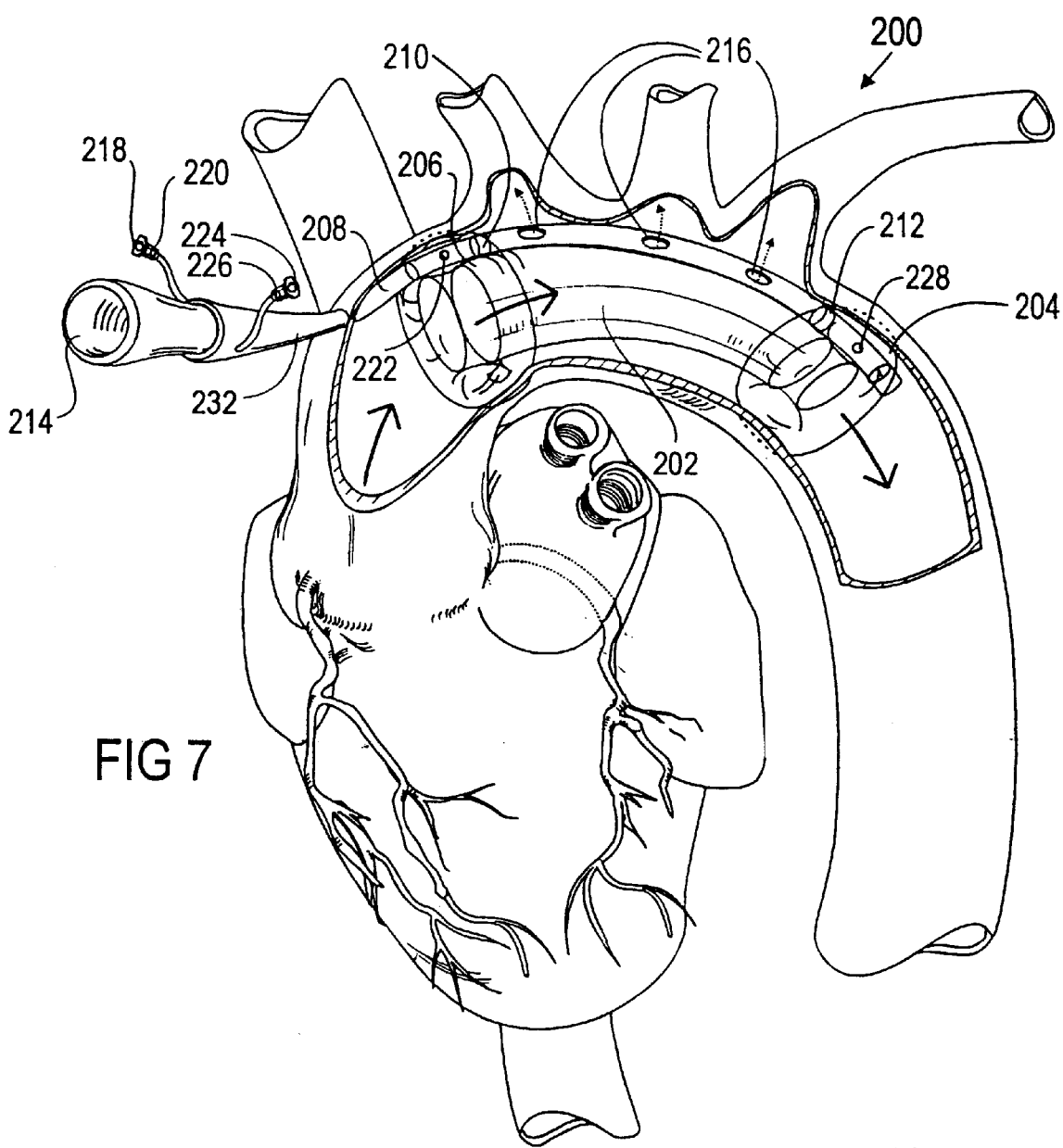
FIGS. 7 and 8 show an aortic perfusion shunt apparatus configured for antegrade deployment via direct aortic insertion.
Figure 8:
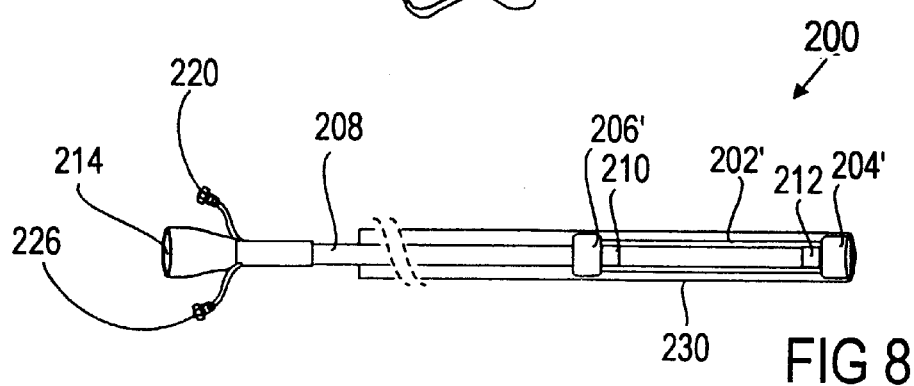

FIGS. 7 and 8 show an aortic perfusion shunt apparatus 200 configured for antegrade deployment via direct aortic insertion. FIG. 7 is a cutaway perspective view of the perfusion shunt apparatus 200 deployed with the perfusion shunt conduit 202 in an expanded state within the aorta. FIG. 8 shows the apparatus 200 with the perfusion shunt conduit 202' in a collapsed state for insertion or withdrawal of the device from the aorta.

The perfusion shunt conduit 202 is mounted on an elongated catheter shaft 208. The perfusion shunt conduit 202 is similar to the embodiments previously described except that, because the aortic perfusion shunt apparatus 200 is introduced into the ascending aorta in the antegrade direction, the upstream sealing member 206 is positioned proximally to the downstream sealing member 204 on the elongated catheter shaft 208. The elongated catheter shaft 208 has a perfusion lumen 214 which is fluidly connected to one or more perfusion ports 216 located on the catheter shaft 208 between the upstream sealing member 206 and the downstream sealing member 204. The proximal end of the elongated catheter shaft 208 is adapted for connecting the perfusion lumen 214 to a cardiopulmonary bypass pump or other source of oxygenated blood or other fluid using standard barb connectors or other connectors. A first inflation lumen 218 fluidly connects a first luer fitting 220 with a first inflation port 222 located on the interior of the upstream sealing member 206. A second inflation lumen 224 fluidly connects a second luer fitting 226 with a second inflation port 228 located on the interior of the downstream sealing member 204. Optionally, the elongated catheter shaft 208 may also include a second perfusion lumen (not shown), which would be connected to one or more perfusion ports located upstream of the upstream sealing member 206.

The perfusion lumen 214 should be configured to allow sufficient fluid flow to preserve organ and tissue function of the organs and tissues supplied by the target branch vessels. Because the perfusion shunt apparatus 200 is introduced directly into the ascending aorta, the elongated catheter shaft 208 can be reduced to a length of approximately 20 to 60 cm and an outside diameter of approximately 6 to 12 French size (2 to 4 mm outside diameter) for delivering the 0.25 to 1.5 liters per minute of oxygenated blood needed to perfuse the arch vessels to preserve organ function.

Preferably, the perfusion shunt apparatus 200 includes a first, upstream radiopaque and/or sonoreflective marker ring 210 on the catheter shaft 208 just distal to the upstream sealing member 206 and a second, downstream radiopaque and/or sonoreflective marker ring 212 on the catheter shaft 208 just proximal to the downstream sealing member 204. Visual markers may also be placed on the catheter shaft 208 to assist placement under direct or thoracoscopic visualization.

In use, a purse string suture is placed in the wall of the ascending aorta and an aortotomy incision is made. The perfusion shunt apparatus 200 is introduced into the ascending aorta through the aortotomy incision, with the perfusion shunt conduit 202', upstream sealing member 206' and the downstream sealing member 204' in a collapsed state, as shown in FIG. 8. Optionally, the collapsed perfusion shunt conduit 202' may be covered with an outer tube 230 to ease insertion of the device and to prevent premature deployment. The perfusion shunt apparatus 200 is advanced across the aortic arch in an antegrade fashion. The position of the perfusion shunt apparatus 200 may be monitored using fluoroscopy or ultrasound, such as transesophageal echography (TEE). When the upstream marker 210 is positioned in the ascending aorta between the aortic valve and the brachiocephalic artery and the downstream marker 212 is positioned downstream of the left subclavian artery, the outer tube 230 is withdrawn and the shunt conduit 202 is expanded by inflating the upstream sealing member 206 and the downstream sealing member 204, as shown in FIG. 7. In one preferred embodiment, the catheter shaft 208 has a preformed bend 232 proximal to the perfusion shunt conduit 202 where the catheter shaft 208 passes through the aortic wall to assist seating the apparatus 200 in the correct position. Once the perfusion shunt apparatus 200 is deployed, oxygenated blood or another chosen perfusate may be infused through a perfusion lumen 214 and out thorough the perfusion ports 216 to selectively perfuse the arch vessels. If the perfusion shunt apparatus 200 is to be used in conjunction with cardiopulmonary bypass, an arterial return cannula (not shown) may be placed in the ascending aorta upstream of the shunt conduit 202 using known methods or the aorta may be perfused through the optional second perfusion lumen discussed above. Blood flow through the aortic lumen from the beating heart and/or from the arterial return cannula is shunted past the arch vessels through the internal lumen of the shunt conduit 202. For complete cardiopulmonary bypass with cardioplegic arrest, the perfusion shunt apparatus 200 may be used in combination with a standard aortic cross clamp or with an intra aortic balloon clamp. After use, the shunt conduit 202 is returned to the collapsed position by deflating the upstream sealing member 206 and the downstream sealing member 204 and advancing the outer tube 230 distally over the shunt conduit 202, then the apparatus 200 is withdrawn from the patient.

Figure 9A:
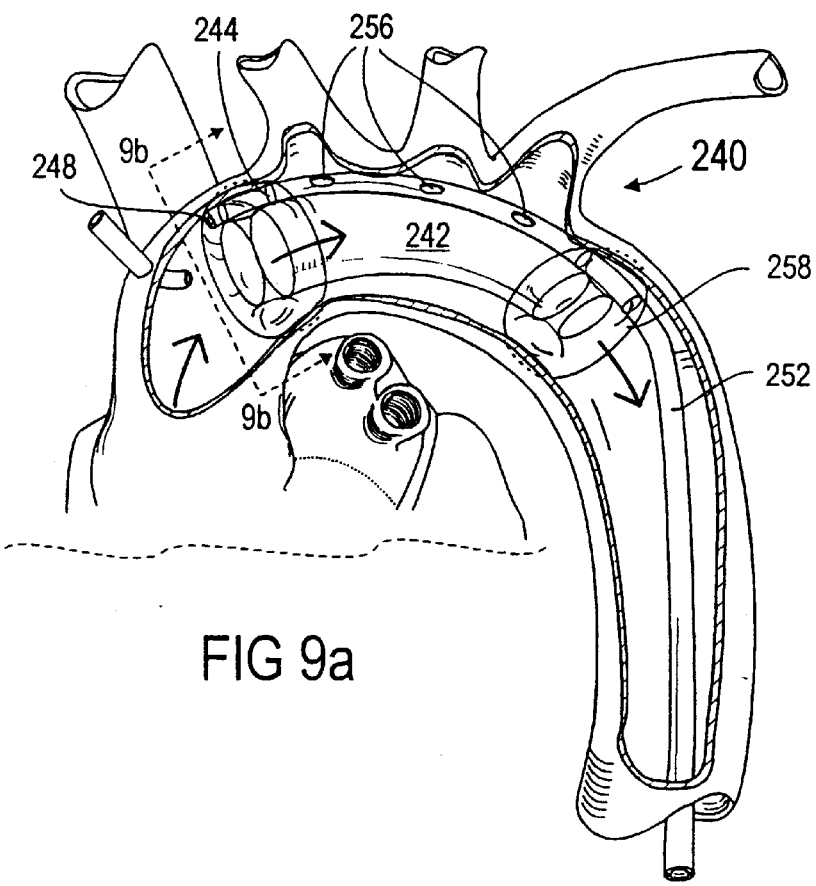
FIGS. 9a–9b and 10a–10b shows an embodiment of an aortic perfusion shunt apparatus with an aortic occlusion mechanism at the upstream end of the shunt conduit.
Figure 9B:
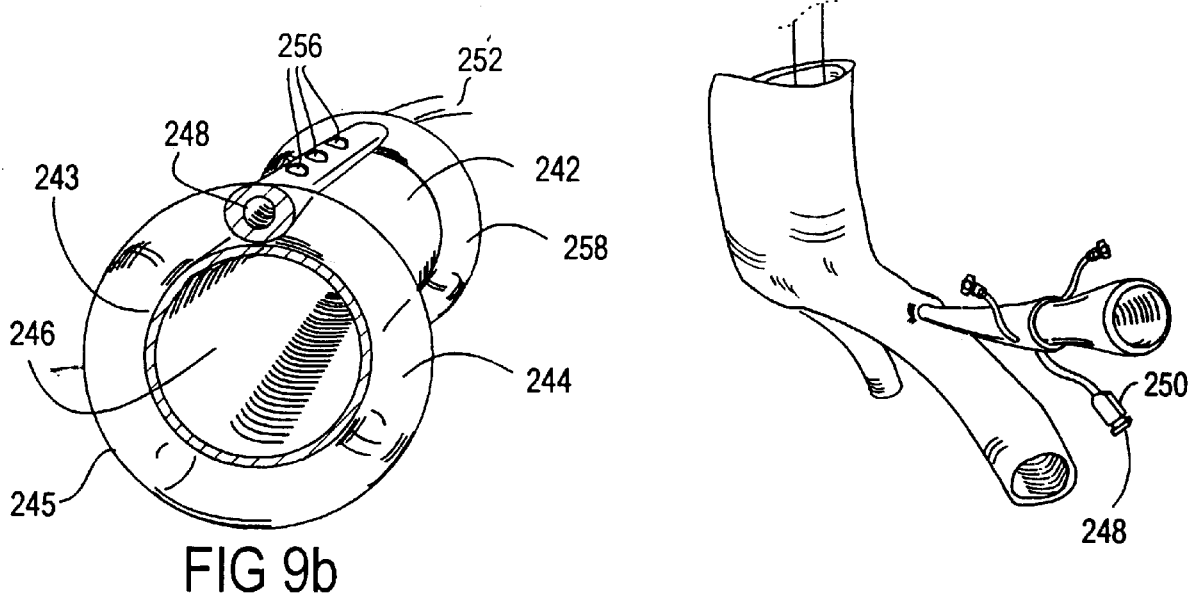
Figure 10A:
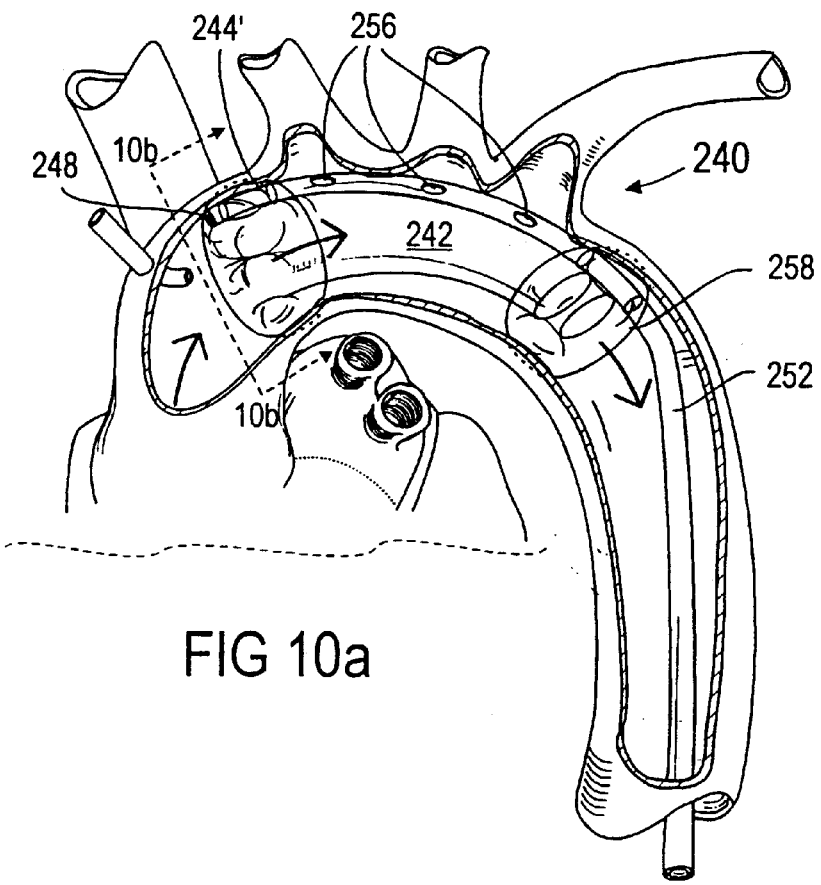
Figure 10B:
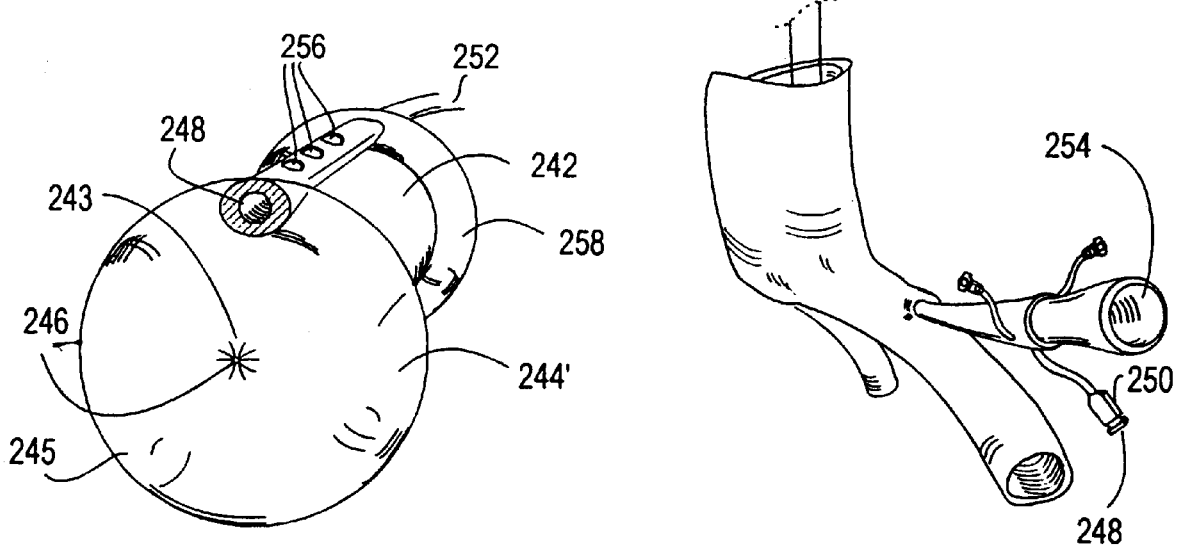

FIGS. 9a–9b and 10a–10b show an embodiment of an aortic perfusion shunt apparatus 240 with an aortic occlusion mechanism at the upstream end of the expandable shunt conduit 242. FIG. 9a shows the aortic perfusion shunt apparatus 240 with the expandable shunt conduit 242 deployed within a patient's aortic arch. FIG. 9b is a distal end view of the expandable shunt conduit 242 of the aortic perfusion shunt apparatus 240 of FIG. 9a. FIG. 10a shows the aortic perfusion shunt apparatus 240 of FIG. 9a with the aortic occlusion mechanism 244' activated to block flow through the expandable shunt conduit 242. FIG. 10b is a distal end view of the expandable shunt conduit 242 and activated aortic occlusion mechanism 244' of FIG. 10a.

This embodiment of the aortic perfusion shunt apparatus 240 may be adapted for retrograde deployment via peripheral arterial access, as shown, or it may be adapted for antegrade deployment via direct aortic insertion. In most aspects, the aortic perfusion shunt apparatus 240 and the expandable shunt conduit 242 are similar in construction to the embodiments previously described. However, the upstream sealing member 244 is adapted so that it also serves as an aortic occlusion mechanism. The upstream sealing member 244 is expandable from a collapsed position for insertion to an expanded position for sealing between the expandable shunt conduit 242 and the aortic wall, as shown in FIGS. 9a and 9b. As shown in FIGS. 10a and 10b, the upstream sealing member 244' is further expandable to an occluding position in which the inner diameter of the toroidal upstream sealing member 244' decreases to occlude the inner lumen 246 of the expandable shunt conduit 242. To encourage the upstream sealing member 244' to expand inward to occlude the inner lumen 246 of the expandable shunt conduit 242, the toroidal balloon 244 may be made with differential wall compliance. For example, the toroidal upstream sealing member 144 may be made with a thinner balloon wall 243 near the inner surface of the toroidal balloon and a thicker balloon wall 245 near the outer surface of the toroidal balloon, as indicated in FIG. 10b. Differential wall compliance can also be accomplished by combining different balloon materials of varying elasticity. This integral aortic occlusion mechanism obviates the need for a separate aortic cross clamp or intra aortic balloon clamp when the aortic perfusion shunt apparatus 240 is used for complete cardiopulmonary bypass with cardioplegic arrest. Preferably, the aortic perfusion shunt apparatus 240 also includes a cardioplegia lumen 248, which extends from the distal end of the elongated catheter shaft 252 to a luer fitting 250 on the proximal end. The cardioplegia lumen 248 may also be used as a guidewire lumen to assist introduction of the device into the vasculature.

After the upstream sealing member 244' has been inflated to its occluding position, cardioplegic solution may be infused through the cardioplegia lumen 248 into the aortic root and hence into the coronary arteries to induce cardioplegic arrest. The arch vessels may be selectively perfused through the perfusion lumen 254, which connects to one or more perfusion ports 256 located on the exterior of the catheter shaft 252 between the upstream sealing member 244 and the downstream sealing member 252. The descending aorta downstream of the perfusion shunt apparatus 240 may be perfused through a separate arterial cannula, which may be placed in the contralateral femoral artery or which may be coaxial to the elongated catheter shaft 252. Alternatively, the elongated catheter shaft 252 of the perfusion shunt apparatus 240 may be provided with a second perfusion lumen (not shown) connecting to perfusion ports located downstream of the downstream sealing member 252.

The patient can be converted from cardioplegic arrest to a beating heart condition, while maintaining selective perfusion of the arch vessels, by partially deflating the upstream sealing member from the occluding position 244' to the expanded position 244. This allows oxygenated blood to flow retrograde through the inner lumen 246 of the expandable shunt conduit 242 and into the coronary arteries to revive the arrested heart. Once the heart has resumed beating, blood flow from the heart will flow antegrade through the expandable shunt conduit 242 to the rest of the body. Selective perfusion of the arch vessels through the perfusion lumen 254 may be maintained as long as necessary. After use, the shunt conduit 242 is returned to the collapsed position by deflating the upstream sealing member 244 and the downstream sealing member 252 and the apparatus 240 is withdrawn from the patient.

Figure 11A:
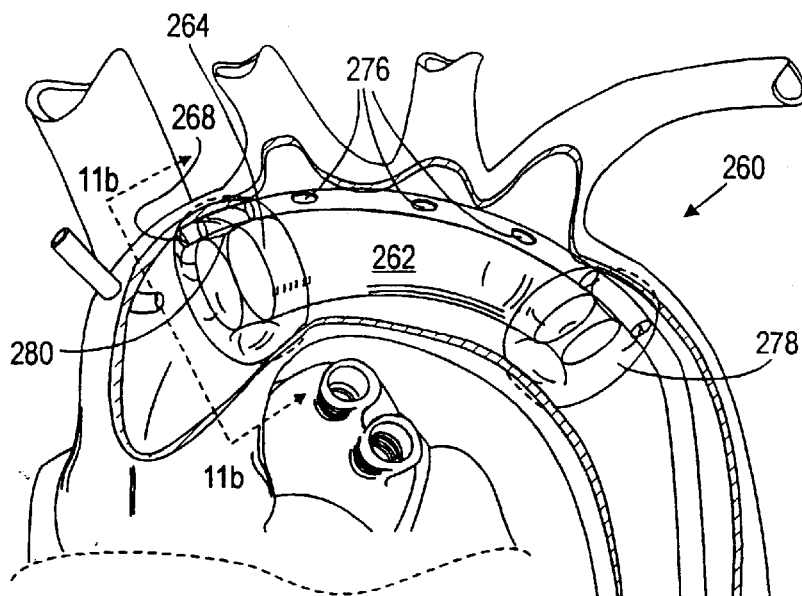
FIGS. 11a–11b and 12a–12b show an alternate embodiment of an aortic perfusion shunt apparatus with an aortic occlusion mechanism at the upstream end of the shunt conduit.
Figure 11B:
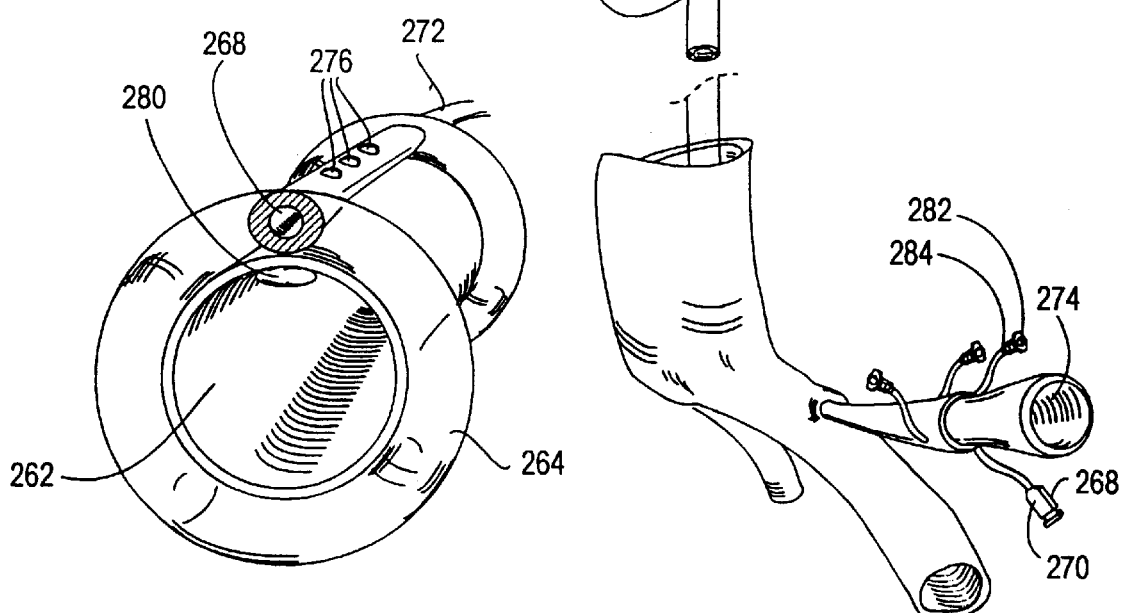
Figure 12A:
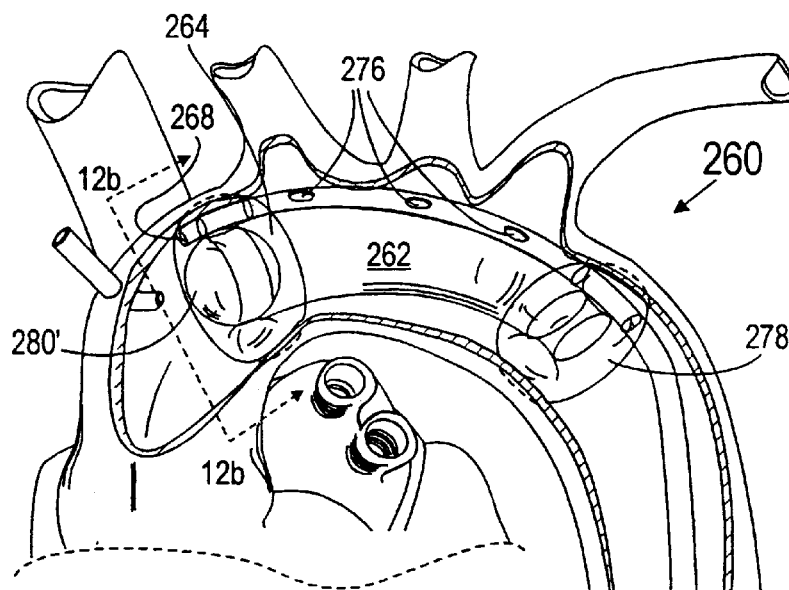
Figure 12B:
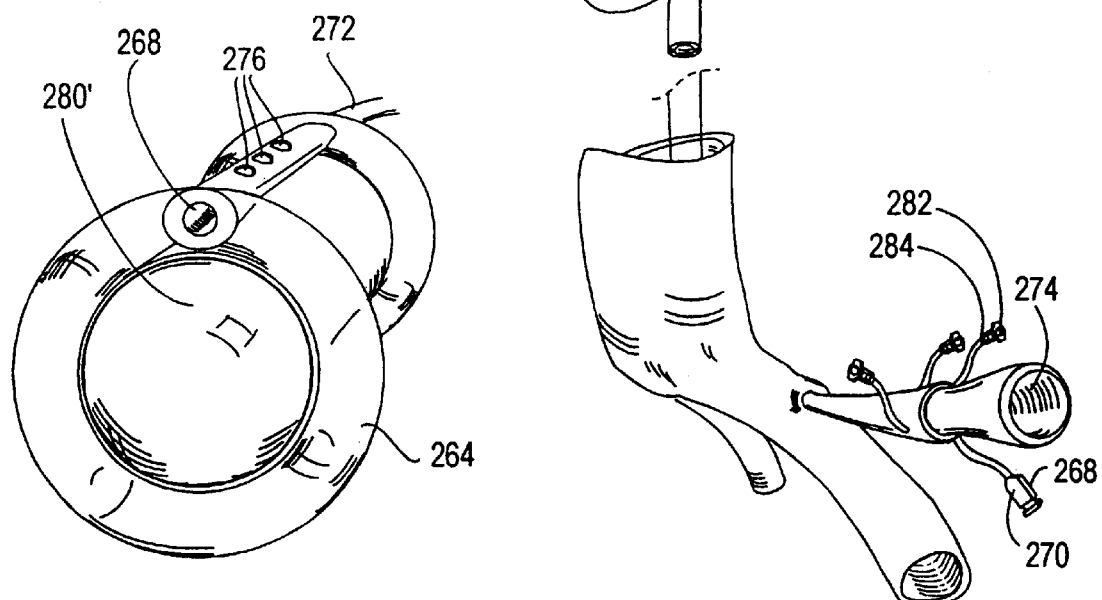

FIGS. 11a–11b and 12a–12b show an alternate embodiment of an aortic perfusion shunt apparatus 260 with an aortic occlusion mechanism 280 at the upstream end of the expandable shunt conduit 262. FIG. 11a shows the aortic perfusion shunt apparatus 260 with the expandable shunt conduit 262 deployed within a patient's aortic arch. FIG. 11b is a distal end view of the expandable shunt conduit 262 of the aortic perfusion shunt apparatus 260 of FIG. 11a. FIG. 12a shows the aortic perfusion shunt apparatus 260 of FIG. 11a with the aortic occlusion mechanism 280' activated to block flow through the expandable shunt conduit 262. FIG. 12b is a distal end view of the expandable shunt conduit 262 and activated aortic occlusion mechanism 280' of FIG. 12a.

Again, most aspects of the aortic perfusion shunt apparatus 260 and the expandable shunt conduit 262 are similar in construction to the embodiments previously described. In addition, however, the aortic perfusion shunt apparatus 260 includes an occlusion member 280 within the inner lumen 266 of the expandable shunt conduit 262. In one preferred embodiment, the occlusion member 280 is an expandable balloon, which may be generally spherical in shape and may be made of a flexible polymer or elastomer, such as polyvinylchloride, polyurethane, polyethylene, polypropylene, polyamides (nylons), polyester, latex, silicon, or alloys, copolymers and reinforced composites thereof. The occlusion member 280 is fluidly connected by an inflation lumen 282 to a luer fitting 284 or other connector on the proximal end of the perfusion shunt apparatus 260. The occlusion member 280 is inflatable from a collapsed position 280, shown in FIG. 11b, to an occluding position 280', shown in FIG. 12b, to occlude the inner lumen 266 of the expandable shunt conduit 262. Alternatively, the occlusion member 280 may be a flap or valve, which is selectively actuatable to occlude the inner lumen 266 of the expandable shunt conduit 262. This integral aortic occlusion mechanism obviates the need for a separate aortic cross clamp or intra aortic balloon clamp when the aortic perfusion shunt apparatus 260 is used for complete cardiopulmonary bypass with cardioplegic arrest. Preferably, the aortic perfusion shunt apparatus 260 also includes a cardioplegia lumen 268, which extends from the distal end of the elongated catheter shaft 272 to a luer fitting 270 on the proximal end. The cardioplegia lumen 268 may also be used as a guidewire lumen to assist introduction of the device into the vasculature.

After the occlusion member 280' has been inflated to its occluding position, cardioplegic solution may be infused through the cardioplegia lumen 268 into the aortic root and hence into the coronary arteries to induce cardioplegic arrest. The arch vessels may be selectively perfused through the perfusion lumen 274, which connects to one or more perfusion ports 276 located on the exterior of the catheter shaft 272 between the upstream sealing member 264 and the downstream sealing member 272. The descending aorta downstream of the perfusion shunt apparatus 260 may be perfused through a separate arterial cannula, which may be placed in the contralateral femoral artery or which may be coaxial to the elongated catheter shaft 272. Alternatively, the elongated catheter shaft 272 of the perfusion shunt apparatus 260 may be provided with a second perfusion lumen (not shown) connecting to perfusion ports located downstream of the downstream sealing member 272.

The patient can be converted from cardioplegic arrest to a beating heart condition, while maintaining selective perfusion of the arch vessels, by partially or completely deflating the occlusion member 280 from the occluding position 280' to the collapsed position 280. This allows oxygenated blood to flow retrograde through the inner lumen 266 of the expandable shunt conduit 262 and into the coronary arteries to revive the arrested heart. Once the heart has resumed beating, blood flow from the heart will flow antegrade through the expandable shunt conduit 262 to the rest of the body. Selective perfusion of the arch vessels through the perfusion lumen 274 may be maintained as long as necessary. After use, the shunt conduit 262 is returned to the collapsed position by deflating the upstream sealing member 264 and the downstream sealing member 272 and the apparatus 260 is withdrawn from the patient.

FIGS. 13, 14a and 14b show an alternate construction of an aortic perfusion shunt apparatus 290 according to the present invention. FIG. 13 shows the aortic perfusion shunt apparatus 290 deployed within a patient's aorta. FIG. 14a is an end view of the aortic perfusion shunt apparatus 290 of FIG. 13. FIG. 14b is a cross section of the aortic perfusion shunt apparatus 290 of FIG. 13. This alternate construction may be used with any of the embodiments of the perfusion shunt apparatus described herein. In most respects, the aortic perfusion shunt apparatus 290 and the expandable shunt conduit 292 are similar in construction to the embodiments previously described. However, in this embodiment a distal portion of the elongated catheter shaft 294 passes through the inner lumen 296 of the expandable shunt conduit 292. One or more perfusion ports connect to the catheter shaft 294 through the wall of the expandable shunt conduit 292. This construction of the aortic perfusion shunt apparatus 290 allows the expandable shunt conduit 292 to be made in a larger diameter, more closely approximating the luminal diameter of the host vessel, in this case the aortic arch. It also allows a clear unobstructed flow of perfusate around the exterior of the expandable shunt conduit 292. This aspect may be important for other clinical applications where the target branch vessels are distributed around the host vessel rather than lined up along one side of the host vessel, such as in the descending aorta.

Figure 15:
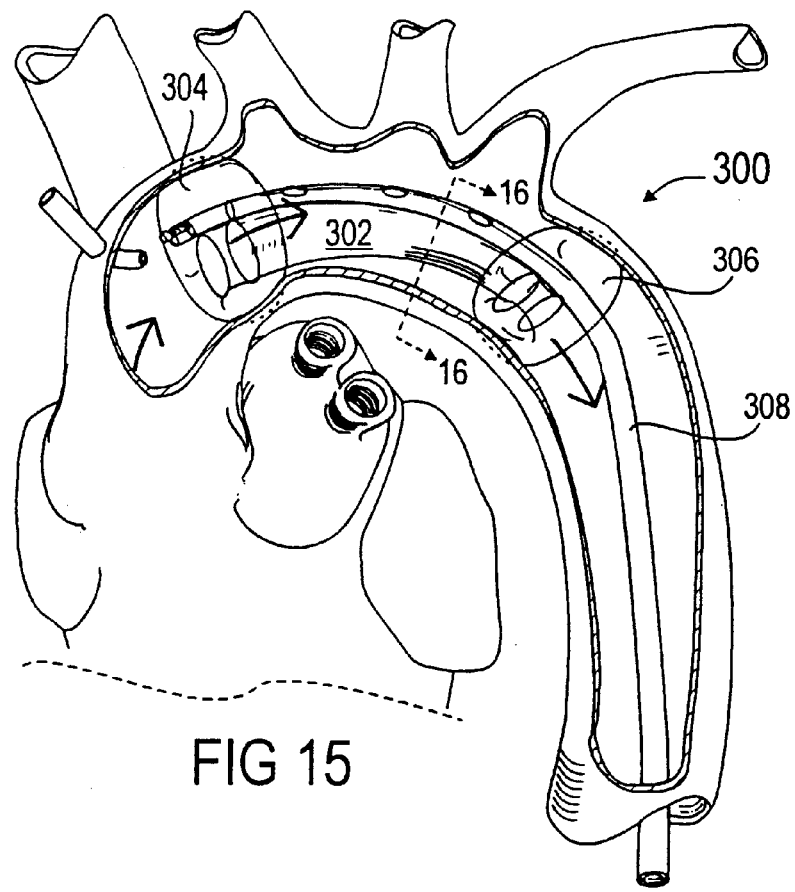
FIG. 15 shows another alternate construction of an aortic perfusion shunt apparatus according to the present invention.
Figure 16:
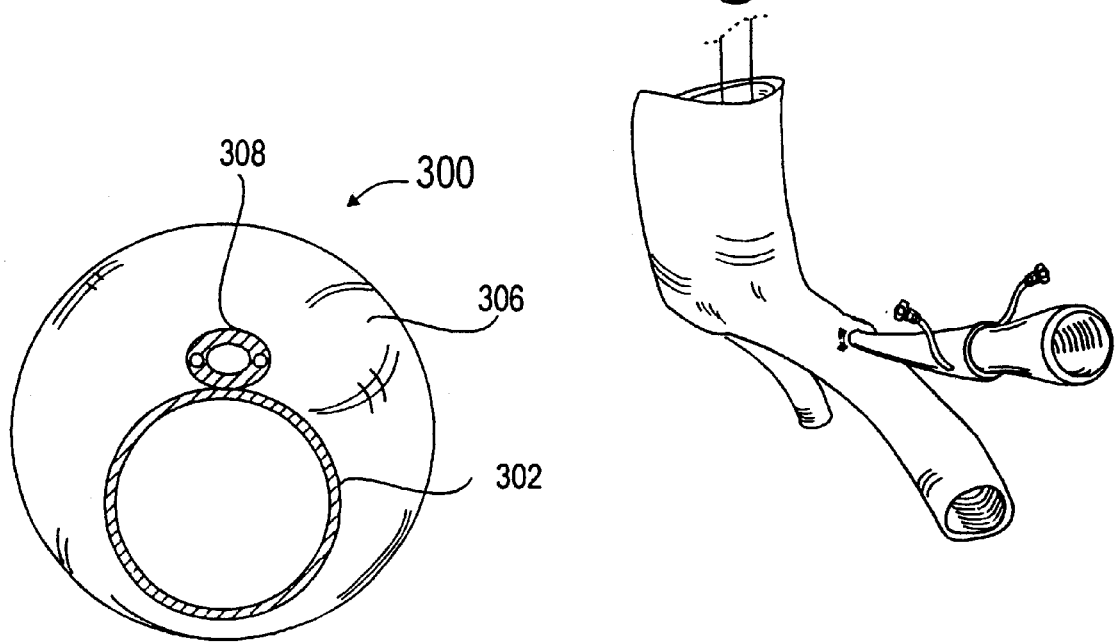
FIG. 16 is a cross section of the aortic perfusion shunt apparatus of FIG. 15.

FIGS. 15 and 16 show another alternate construction of an aortic perfusion shunt apparatus 300 according to the present invention. FIG. 15 shows the aortic perfusion shunt apparatus 300 deployed within a patient's aorta. FIG. 16 is a cross section of the aortic perfusion shunt apparatus 300 of FIG. 15. Once again, this alternate construction may be used with any of the embodiments of the perfusion shunt apparatus described herein. In most respects, the aortic perfusion shunt apparatus 300 and the expandable shunt conduit 302 are similar in construction to the embodiments previously described. However, in this embodiment the upstream sealing member 304 and the downstream sealing member 306 are eccentric toroidal balloon cuffs with the larger side of the eccentric toroidal balloon cuffs positioned toward the arch vessels on the superior side of the aortic arch. This displaces the expandable shunt conduit 302 and the elongated catheter shaft 308 toward the inferior side of the aortic arch and away from the arch vessels. The expandable shunt conduit 302 and the elongated catheter shaft 308 are thus less likely to interfere with blood flow into the arch vessels when the aortic perfusion shunt apparatus 300 is deployed.

Figure 17:
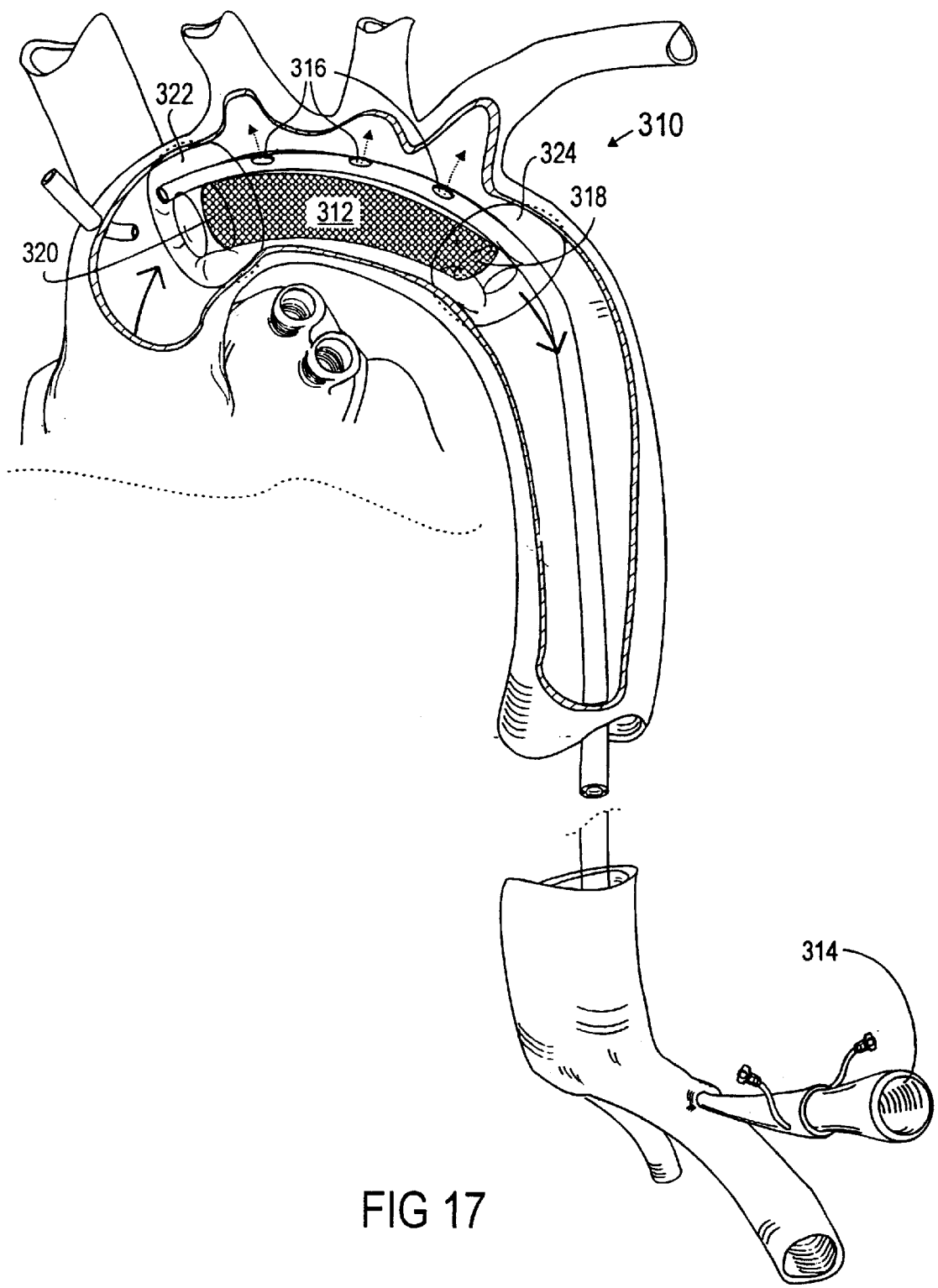
FIG. 17 shows an aortic perfusion filter shunt apparatus according to the present invention.

FIG. 17 shows an aortic perfusion filter shunt apparatus 310 according to the present invention. In most respects, the aortic perfusion shunt apparatus 310 and the expandable shunt conduit 312 are similar in construction to the embodiments previously described. However, in this embodiment, rather than being made of a relatively impermeable material, the expandable shunt conduit 312 is made of a porous filter mesh material. Optionally the downstream end of the expandable shunt conduit 312 may have an end wall 318 of filter mesh material across the inner lumen 320 of the expandable shunt conduit 312, as well. The filter mesh material of the expandable shunt conduit 312 may be a woven or knitted fabric, such as Dacron or nylon mesh, or other fabrics, or it may be a nonwoven fabric, such as a spun bonded polyolefin or expanded polytetrafluoroethylene or other nonwoven material. Alternatively, the filter mesh material of the expandable shunt conduit 312 may be an open cell foam material. The filter mesh material of the expandable shunt conduit 312 must be nontoxic and hemocompatible, that is, non-thrombogenic and non-hemolytic. Preferably, the filter mesh material of the expandable shunt conduit 312 has a high percentage of open space, with a uniform pore size. The pore size of the filter mesh material can be chosen to capture macroemboli only or to capture macroemboli and microemboli. In most cases the pore size of the filter mesh material will preferably be in the range of 1–200 micrometers. For capturing macroemboli only, the pore size of the filter mesh material will preferably be in the range of 50–200 micrometers, more preferably in the range of 80–100 micrometers. For capturing macroemboli and microemboli, the pore size of the filter mesh material will preferably be in the range of 1–100 micrometers, more preferably in the range of 5–20 micrometers. In other applications, such as for treating thromboemolic disease, a larger pore size, e.g. up to 1000 micrometers (1 mm) or larger, would also be useful. In some embodiments, a combination of filter materials having different pore sizes may be used. The expandable shunt conduit 312 and the end wall 318 may be made of filter mesh materials having different pore sizes. For example, the expandable shunt conduit 312 may be made with a very fine filter mesh material for capturing both macroemboli and microemboli, and the end wall 318 may be made of a coarser filter mesh material for capturing macroemboli only.

When the aortic perfusion filter shunt apparatus 310 is deployed within the aortic arch, the filter mesh material of the expandable shunt conduit 312 will protect the arch vessels and prevent emboli from entering the cerebral vasculature. Potential emboli that are stopped by the filter mesh material of the expandable shunt conduit 312 will either pass through the inner lumen 320 of the expandable shunt conduit 312 and flow downstream where they will be better tolerated or they will be stopped by the filter mesh material of the end wall 318. Undesirable embolic events can be avoided without stopping the heart or otherwise interfering with the normal function of the circulatory system. In addition, selective perfusion of the arch vessels with a perfusate of preselected temperature or chemical composition can be performed through the perfusion lumen 314 of the aortic perfusion filter shunt apparatus 310. The perfusate that exits the perfusion ports 316 will be concentrated in the arch vessels by the presence of the filter mesh material of the expandable shunt conduit 312.

In addition, the aortic perfusion filter shunt apparatus 310 of FIG. 17 may be combined with the aortic occlusion mechanism of FIGS. 9a–9b and 10a–10b or 11a–11b and 12a–12b for performing complete cardiopulmonary bypass with cardioplegic arrest. With this arrangement, one catheter will provide a motionless stopped heart environment for intricate cardiac surgery while on bypass and cerebrovascular protection by filtration an selective perfusion while on or off bypass.

Additionally or alternatively, the aortic perfusion filter shunt apparatus 310 of FIG. 17 may be operated in the alternate method of use described above in connection with FIGS. 1–3 by inflating the upstream sealing member 322 only to expand the shunt conduit 312 and leaving the downstream sealing member 324 uninflated. The annular space around the expandable shunt conduit 312 is perfused through the perfusion ports 316 of the perfusion lumen 314. When using this alternate method, the aortic perfusion filter shunt apparatus 310 may be simplified by eliminating the downstream sealing member 324 from the shunt conduit 312.

Figure 18:
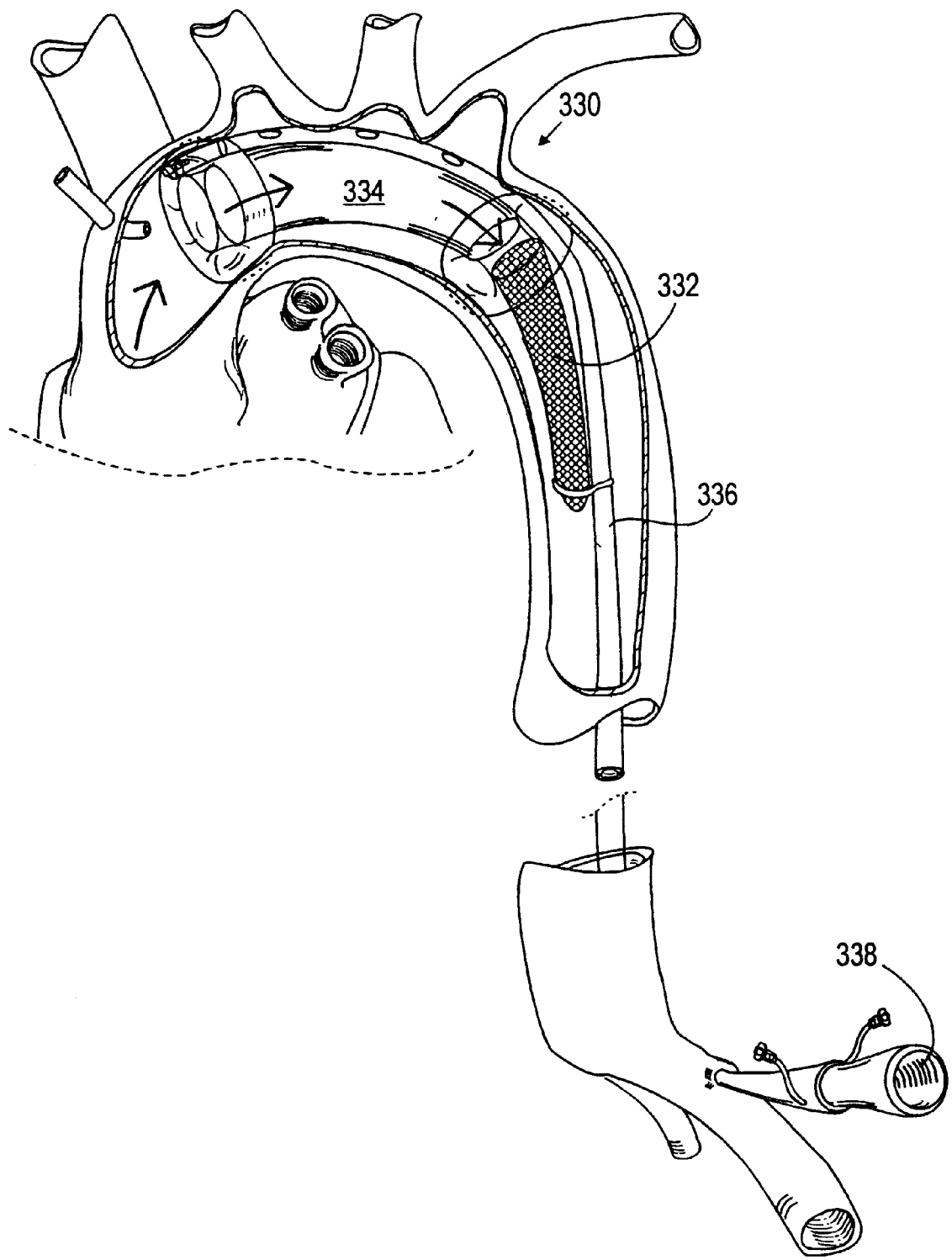
FIG. 18 shows a combined aortic perfusion shunt apparatus with an embolic filter mechanism positioned at the downstream end of the shunt conduit.

FIG. 18 shows a combined aortic perfusion shunt apparatus 330 with an embolic filter mechanism 332 positioned at the downstream end of the shunt conduit. The elongated catheter shaft 336 and the expandable shunt conduit 312 of the apparatus 330 may be built according to any of the previously described embodiments. Attached to the apparatus 330 at the downstream end of the expandable shunt conduit 312 is an embolic filter mechanism 332 made of a filter mesh material. The filter mesh material of the embolic filter mechanism 332, which may be made of any of the filter materials described above, can be chosen to capture macroemboli only or to capture macroemboli and microemboli. The embolic filter mechanism 332 may be roughly conical in shape as shown or any other convenient geometry. Other examples of suitable geometries and constructions for the embolic filter mechanism 332 may be found in commonly owned, copending U.S. provisional application 60/060,117, and corresponding U.S. patent application Ser. No. 09/158, 405, which has previously been incorporated by reference.

When the aortic perfusion shunt apparatus 330 is deployed within the aortic arch, the arch vessels and thus the cerebral vasculature, are protected from embolization or hypoperfusion by selective perfusion through the perfusion lumen 338 of the elongated catheter shaft 336, while the organs and tissues downstream of the apparatus 330 are protected from embolization by the embolic filter mechanism 332. In addition, the aortic perfusion shunt apparatus 330 of FIG. 18 may be combined with the aortic occlusion mechanism of FIGS. 9a–9b and 10a–10b or 11a–11b and 12a–12b for performing complete cardiopulmonary bypass with cardioplegic arrest. Thus, one catheter will provide a motionless stopped heart environment for intricate cardiac surgery while on bypass and cerebrovascular protection by filtration and selective perfusion while on or off bypass.

Figure 19:
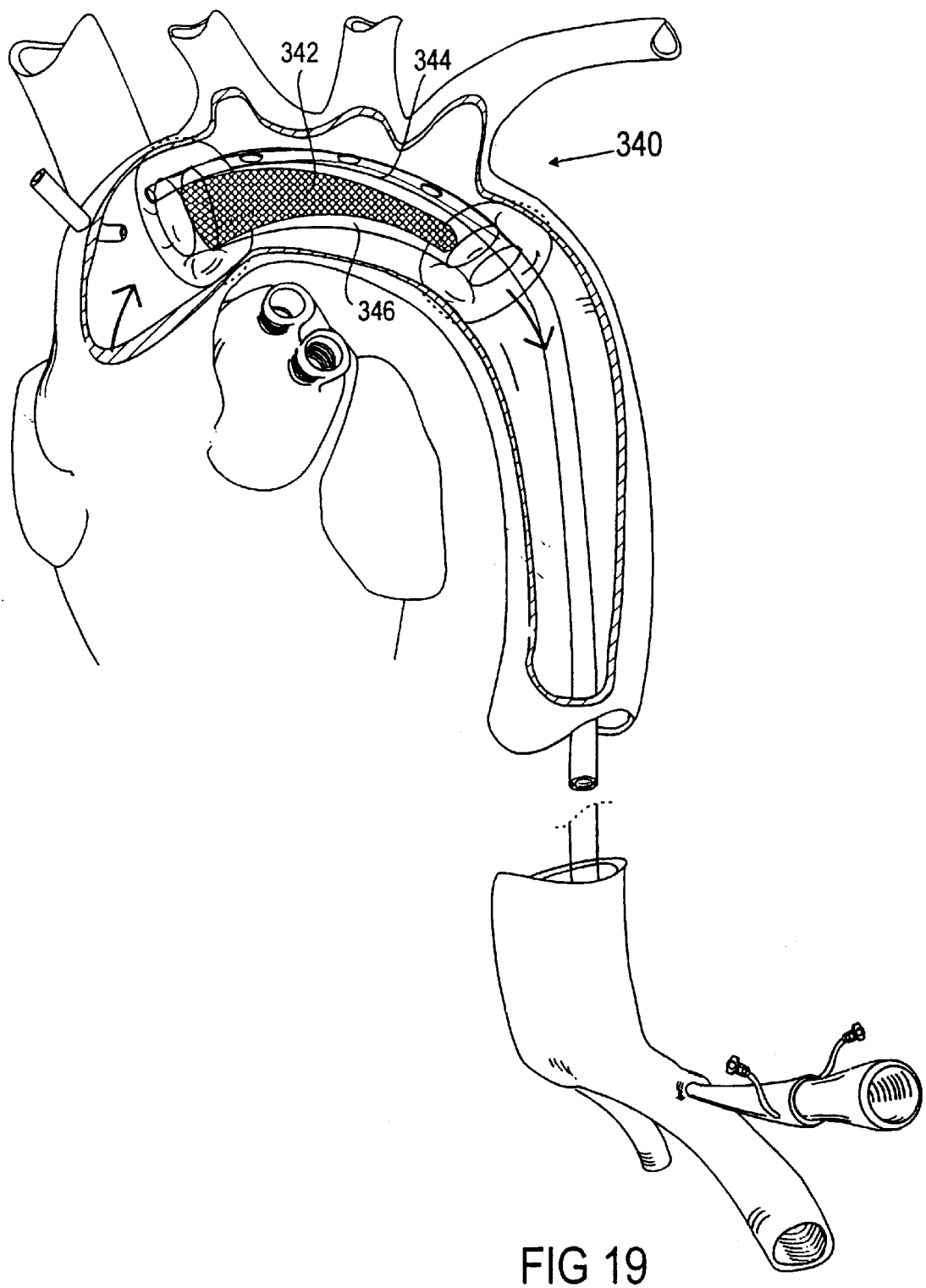
FIG. 19 shows an alternate embodiment of an aortic perfusion shunt apparatus combined with an embolic filter mechanism positioned within the shunt conduit.

FIG. 19 shows an alternate embodiment of an aortic perfusion shunt apparatus 340 combined with an embolic filter mechanism 342 positioned within the expandable shunt conduit 344. This embodiment is similar in construction and materials to the combined aortic perfusion shunt apparatus and embolic filter mechanism of FIG. 16, except that the embolic filter mechanism 342 is positioned within the inner lumen 346 of the expandable shunt conduit 344. This arrangement provides a more compact construction of the apparatus 340. The arrangement also provides additional protection and support for the embolic filter mechanism 342, which can thus be made of very delicate or intricately arranged fine filter mesh material. The additional protection also provides more positive capture of embolic materials within the embolic filter mechanism 342, particularly upon withdrawal of the device after use, because the filter mesh material of the embolic filter mechanism 342 is surrounded with the relatively impermeable material of the expandable shunt conduit 344. The apparatus of FIG. 19 can also be combined with any of the embodiments or constructions previously described in conjunction with other embodiments of the present invention, including the aortic occlusion mechanisms of FIGS. 9a–9b and 10a–10b or 11a–11b and 12a–12b. Likewise, all operable combinations and subcombinations of the features of the present invention described herein, or incorporated by reference, are considered to be within the scope of the present invention whether or not they have been explicitly described.

Figure 20:
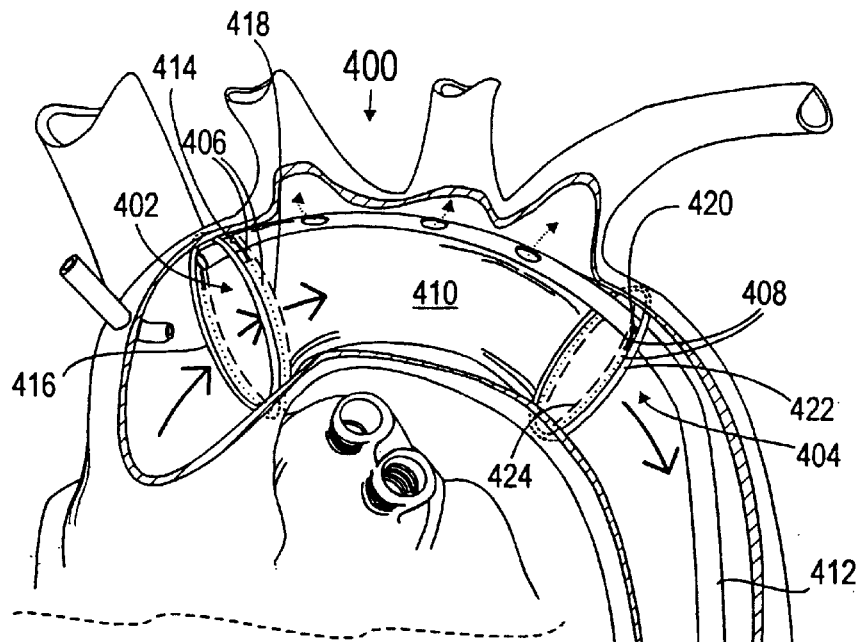
FIGS. 20 and 21 show an aortic perfusion shunt apparatus configured for retrograde deployment via femoral artery access and having upstream and downstream sealing members operated by extendible and retractable elongated expansion members.
Figure 21:
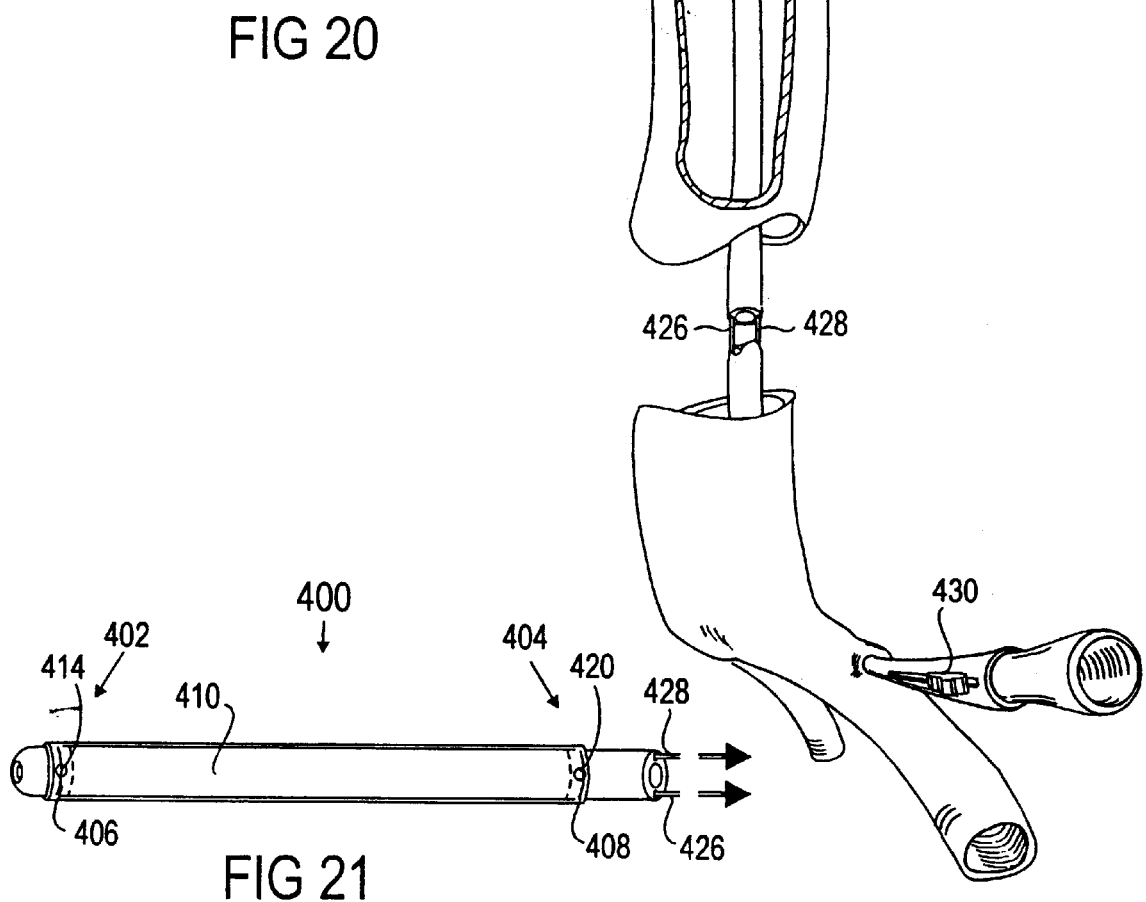

FIGS. 20 and 21 show an aortic perfusion shunt apparatus 400 configured for retrograde deployment via femoral artery access and having upstream and downstream sealing members 402, 404 operated by extendible and retractable elongated expansion members 406, 408. FIG. 20 is a cutaway perspective view of the perfusion shunt apparatus 400 deployed within the aorta. FIG. 21 shows the apparatus with the perfusion shunt conduit 410 in a collapsed state for insertion or withdrawal of the device from the patient.

Similar to the previously described embodiments, the aortic perfusion shunt apparatus 400 has an elongated catheter or cannula shaft 412 that may be configured for introduction via peripheral artery access, as shown, or for central aortic access. An expandable shunt conduit 410 is mounted near the distal end of the catheter shaft 412. The expandable shunt conduit 410 is a tubular structure of either porous or impermeable fabric. An upstream elongated expansion member 406 extends out of a port or ports 414 on the catheter shaft 412 and encircles the shunt conduit 410 near its upstream end 416. The fabric of the shunt conduit 410 is folded back over the upstream elongated expansion member 406 and sewn with a seam 418 to enclose the upstream elongated expansion member 406. A downstream elongated expansion member 408 extends out of another port or ports 420 on the catheter shaft 412 and encircles the shunt conduit 410 near its downstream end 422. The fabric of the shunt conduit 410 is folded back over the downstream elongated expansion member 408 and sewn with a seam 424 to enclose the downstream elongated expansion member 408.

The upstream elongated expansion member 406 is a flexible wire, rod, fiber or cable made from a polymer or metal, such as stainless steel or a nickel-titanium alloy. A first actuation member 426 extends through the catheter shaft 412 and connects the upstream elongated expansion member 406 to a first actuator button 430 on the proximal end of the perfusion shunt apparatus 400. The first actuation member 426 may be an extension of the upstream elongated expansion member 406 or it may be a separate wire or rod attached to the upstream elongated expansion member 406.

Similarly, the downstream elongated expansion member 408 is a flexible wire, rod, fiber or cable made from a polymer or metal, such as stainless steel or a nickel-titanium alloy. A second actuation member 428 extends through the catheter shaft 412 and connects the downstream elongated expansion member 408 to a second actuator button (not visible in this view) on the proximal end of the perfusion shunt apparatus 400. The second actuation member 428 may be an extension of the downstream elongated expansion member 408 or it may be a separate wire or rod attached to the downstream elongated expansion member 408. Alternatively, the upstream elongated expansion member 406 and the downstream elongated expansion member 408 may be actuated by a single actuation member 426 and actuator button 430.

To prepare the aortic perfusion shunt apparatus 400 for use, the actuator button or buttons 430 are moved proximally to retract the upstream elongated expansion member 406 and the downstream elongated expansion member 408 into the catheter shaft 412 through the ports 414, 420. This gathers the upstream end 416 and the downstream end 422 of the shunt conduit 410 and collapses the shunt conduit 410 toward the catheter shaft 412, as shown in FIG. 21. Optionally, an outer tube (not shown) may be placed over the collapsed shunt conduit 410.

The aortic perfusion shunt apparatus 400 is inserted and positioned as previously described. Once the aortic perfusion shunt apparatus 400 is in the proper position, the process is reversed to deploy the expandable shunt conduit 410. The actuator button or buttons 430 are moved distally to extend the upstream elongated expansion member 406 and the downstream elongated expansion member 408 from the ports 414, 420 in the catheter shaft 412. This expands the upstream end 416 and the downstream end 422 of the shunt conduit 410 until they contact and create a seal against the inner surface of the aorta, as shown in FIG. 20. Advantageously, the shunt conduit 410 maybe made of a somewhat elastic film or fabric to easily accommodate variations in the sizes of patient's aortas.

As in previously described embodiments, the aortic perfusion shunt apparatus 400 of FIGS. 20 and 21 may optionally include one or more radiopaque and/or sonoreflective markers on the apparatus for enhanced imaging by fluoroscopic or ultrasonic imaging techniques. Another feature that can be combined with each of the embodiments of the present invention is an aortic transillumination system for locating and monitoring the position of the catheter, the shunt and the optional occlusion devices without fluoroscopy by transillumination of the aortic wall. Aortic transillumination systems using optical fibers and/or light emitting diodes or lasers suitable for this application are described in commonly owned, copending U.S. patent application Ser. No. 60/088,652, filed Jun. 9, 1998, which is hereby incorporated by reference in its entirety. By way of example, the aortic perfusion shunt apparatus 400 of FIGS. 20 and 21 is easily adaptable for use with a fiberoptic system for aortic transillumination. For this purpose, the upstream elongated expansion member 406 and the first actuation member 426 may be made of a first optical fiber, preferably a flexible polymeric optical fiber. Similarly, the downstream elongated expansion member 408 and the second actuation member 428 may be made of a second optical fiber, also preferably a flexible polymeric optical fiber. An optical coupling (not shown) would be provided at the proximal end of the perfusion shunt apparatus 400 to connect the optical fibers to a light source. The fiberoptic upstream elongated expansion member 406 and the fiberoptic downstream elongated expansion member 408 can be made lossy by abrading the optical fibers or their cladding so that light escapes through the walls of the fibers. The light emitted by the fiberoptic upstream elongated expansion member 406 and the fiberoptic downstream elongated expansion member 408 is visible through the aortic wall and can be used to locate and monitor the position and the deployment state of the expandable shunt conduit 410. Similarly, in embodiments of the perfusion shunt apparatus utilizing an aortic occlusion device, one or more optical fibers or other light emitting devices may be positioned on the aortic occlusion device to locate and monitor its position and state of deployment.

Likewise, the features and embodiments of the present invention may also be combined with a bumper location device for facilitating catheter insertion and positioning by providing tactile feedback when the catheter device contacts the aortic valve. Bumper location devices suitable for this application are described in commonly owned, copending U.S. provisional patent applications 60/060,158, filed Sep. 26, 1997, and 60/073,681, filed Feb. 4, 1998, and corresponding U.S. patent application Ser. No. 09/161,207, which are hereby incorporated by reference in their entirety.

While the present invention has been described herein with respect to the exemplary embodiments and the best mode for practicing the invention, it will be apparent to one of ordinary skill in the art that many modifications, improvements and subcombinations of the various embodiments, adaptations and variations can be made to the invention without departing from the spirit and scope thereof.

What is claimed is:

1. A catheter apparatus for use in a body passage, comprising:
    a catheter shaft;
    an expandable conduit mounted on said catheter shaft, said expandable conduit having an upstream end, a downstream end and a filter mesh material extending therebetween, said expandable conduit having a collapsed position in which said expandable conduit is collapsed toward said catheter shaft and an expanded position in which said upstream end of said expandable conduit is open to fluid flow;
    an upstream sealing member at said upstream end of said expandable conduit for creating a seal between said upstream end of said expandable conduit and an internal wall of the body passage; and
    a downstream sealing member at said downstream end of said expandable conduit for creating a seal between said downstream end of said expandable conduit and the internal wall of the body passage.

2. The catheter apparatus of claim 1, further comprising a perfusion lumen within said catheter shaft in fluid communication with a space exterior to said expandable conduit.

3. The catheter apparatus of claim 1, wherein said upstream sealing member comprises an inflatable toroidal balloon.

4. The catheter apparatus of claim 3, wherein said downstream sealing member comprises an inflatable toroidal balloon.

5. The catheter apparatus of claim 1, wherein said upstream sealing member comprises an elongated expansion member extendible to expand said upstream end of said expandable shunt conduit.

6. The catheter apparatus of claim 5, wherein said downstream sealing member comprises an elongated expansion member extendible to expand said downstream end of said expandable shunt conduit.

7. The catheter apparatus of claim 1, wherein said upstream sealing member comprises an external flow control valve.

8. The catheter apparatus of claim 7, wherein said downstream sealing member comprises an external flow control valve.

9. The catheter apparatus of claim 1, wherein said downstream sealing member comprises a retrograde flow external flow control valve.

10. The catheter apparatus of claim 9, wherein said upstream sealing member comprises an antegrade flow external flow control valve.

11. The catheter apparatus of claim 1, wherein said expandable shunt conduit further comprises an end wall of porous fabric across said downstream end of said expandable shunt conduit.

12. The catheter apparatus of claim 1, further comprising an occlusion member for selectively occluding a vessel proximate said upstream sealing member.

13. The catheter apparatus of claim 12, further comprising an infusion lumen within said catheter shaft having an infusion port upstream of said occlusion member.

14. The catheter apparatus of claim 13, further comprising a second perfusion lumen within said catheter shaft.

15. The catheter apparatus of claim 1, further comprising a tubular sheath sized to fit over said expandable conduit when in said collapsed position.

16. The catheter apparatus of claim 12, wherein said occlusion member is an inflatable occlusion balloon.

17. The catheter apparatus of claim 1, wherein said catheter shaft is positioned external to said expandable shunt conduit.

18. The catheter apparatus of claim 1, wherein said catheter shaft is positioned internal to said expandable conduit.

19. The catheter apparatus of claim 1, further comprising an end wall of filter mesh material across said downstream end.

20. A catheter apparatus for use in a body passage, comprising:
    a catheter shaft;
    an expandable conduit defined by a filter mesh material of varying porosity mounted on said catheter shaft, said expandable conduit having an upstream end and a downstream end, said expandable conduit having a collapsed position in which said expandable conduit is collapsed toward said catheter shaft and an expanded position in which said upstream end of said expandable conduit is open to fluid flow; and
    an upstream sealing member at said upstream end of said expandable conduit for creating a seal between said upstream end of said expandable conduit and an internal wall of the body passage.

21. The catheter apparatus of claim 20, wherein said upstream sealing member comprises an inflatable toroidal balloon.

22. The catheter apparatus of claim 20, further comprising a perfusion lumen within said catheter shaft in fluid communication with a space exterior to said expandable conduit.

23. The catheter apparatus of claim 20, wherein said upstream sealing member comprises an external flow control valve.

24. The catheter apparatus of claim 20, wherein said expandable conduit further comprises at least one longitudinal support member attached to a wall of said expandable conduit.

25. The catheter apparatus of claim 20, wherein said expandable conduit further comprises an end wall of porous fabric across said downstream end of said expandable conduit.

26. The catheter apparatus of claim 20, further comprising an occlusion member for selectively occluding said expandable conduit.

27. The catheter apparatus of claim 26, further comprising an infusion lumen within said catheter shaft having an infusion port upstream of said occlusion member.

28. The catheter apparatus of claim 20, further comprising a downstream sealing member at said downstream end of said expandable conduit for creating a seal between said downstream end of said expandable conduit and the internal wall of the body passage.

29. The catheter apparatus of claim 22, further comprising a second perfusion lumen within said catheter shaft.

30. The catheter apparatus of claim 20, further comprising a tubular sheath sized to fit over said expandable conduit when in said collapsed position.

31. The catheter apparatus of claim 26, wherein said occlusion member is an inflatable occlusion balloon.

32. The catheter apparatus of claim 20, wherein said catheter shaft is positioned external to said expandable conduit.

33. The catheter apparatus of claim 20, wherein said catheter shaft is positioned internal to said expandable conduit.

34. A method of perfusing a branch vessel in fluid communication with a main vessel in a body of a patient, comprising:
    inserting a perfusion catheter into the main vessel;
    expanding a conduit mounted on said perfusion catheter to open said conduit to fluid flow;
    sealing an upstream end of said expandable conduit to an internal wall of the main vessel upstream of the branch vessel;
    perfusing the branch vessel from a perfusion lumen in fluid communication with a space exterior to said expandable conduit; and
    perfusing the main vessel.

35. The method of claim 34, wherein the step of perfusing the main vessel is accomplished by providing a second perfusion lumen extending through said perfusion catheter.

36. The method of claim 35, further comprising perfusing a cold fluid to the branch vessel.

37. The method of claim 34, wherein the step of perfusing the main vessel is accomplished by a beating heart.

38. The method of claim 34, wherein said expandable conduit is comprised of impermeable material.

39. The method of claim 34, wherein said expandable conduit is comprised of a porous filter material.

40. The method of claim 34, wherein said expandable conduit is comprised of a porous filter material of varying filter porosity.

41. The method of claim 34, further comprising sealing a downstream end of said expandable conduit to an internal wall of the main vessel downstream of the branch vessel.

42. The method of claim 34, wherein said upstream end of said expandable conduit is sealed to the internal wall of the main vessel by inflating a toroidal balloon at said upstream end of said expandable conduit.

43. The method of claim 41, wherein said downstream end of said expandable conduit is sealed to the internal wall of the main vessel by inflating a toroidal balloon at said downstream end of said expandable conduit.

44. The method of claim 34, wherein said upstream end of said expandable conduit is sealed to the internal wall of the main vessel by extending an elongated expansion member to expand said upstream end of said expandable conduit.

45. The method of claim 44, wherein said downstream end of said conduit is sealed to the internal wall of the main vessel by extending an elongated expansion member to expand said downstream end of said expandable conduit.

46. The method of claim 34, wherein said upstream end of said conduit is sealed to the internal wall of the main vessel by an external flow control valve.

47. The method of claim 46, wherein said downstream end of said expandable conduit is sealed to the internal wall of the main vessel by an external flow control valve.

48. The method of claim 34, further comprising occluding said main vessel.

49. The method of claim 44, further comprising infusing fluid into the main vessel upstream of said upstream end of said expandable conduit.

50. The method of claim 49 further comprising infusing a cardioplegic agent into the patient's aorta upstream of said upstream end of said expandable conduit to induce cardioplegic arrest.

51. A catheter apparatus for use in a body passage, comprising:
    a catheter shaft;
    an expandable filter shunt apparatus mounted on said catheter shaft, said expandable filter shunt apparatus having an upstream end, a downstream end and a conduit extending therebetween, said conduit having a collapsed position in which said expandable conduit is collapsed toward said catheter shaft and an expanded position in which said upstream end of said expandable conduit is open to fluid flow;
    an upstream sealing member at said upstream end of said expandable conduit for creating a seal between said upstream end of said expandable conduit and an internal wall of the body passage; and
    a filter downstream of said downstream sealing member.

52. The catheter apparatus of claim 51, further comprising a downstream sealing member at said downstream end of said expandable conduit for creating a seal between said downstream end of said expandable conduit and an internal wall of the body passageway.

53. The catheter apparatus of claim 52, wherein said filter is positioned between said upstream sealing member and said downstream sealing member.

54. The catheter apparatus of claim 51, wherein said filter is positioned downstream of said conduit.

55. The catheter apparatus of claim 54, wherein said conduit is adapted for impermeability of fluid.

56. The aortic catheter of claim 51, wherein said filter is positioned across said downstream sealing member.

57. The catheter apparatus of claim 51, further comprising a perfusion lumen within said catheter shaft in fluid communication with a space exterior to said expandable conduit.

58. The catheter apparatus of claim 57, wherein said perfusion lumen is adapted for coupling to a fluid conditioning apparatus to deliver a conditioned fluid to the patient's arch vessels.

* * * * *